(12) United States Patent
Ochiai

(10) Patent No.: US 9,447,393 B2
(45) Date of Patent: Sep. 20, 2016

(54) PHOSPHATIDIC ACID PHOSPHATASE GENE

(75) Inventor: Misa Ochiai, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 11 days.

(21) Appl. No.: 14/235,146

(22) PCT Filed: Jul. 27, 2012

(86) PCT No.: PCT/JP2012/069172
§ 371 (c)(1),
(2), (4) Date: Jan. 27, 2014

(87) PCT Pub. No.: WO2013/018709
PCT Pub. Date: Feb. 7, 2013

(65) Prior Publication Data
US 2014/0234941 A1 Aug. 21, 2014

(30) Foreign Application Priority Data
Jul. 29, 2011 (JP) .................. 2011-166490

(51) Int. Cl.
*C12N 9/16* (2006.01)
(52) U.S. Cl.
CPC .......... *C12N 9/16* (2013.01); *C12Y 301/03004* (2013.01)
(58) Field of Classification Search
CPC ....................................................... C12N 9/48
See application file for complete search history.

(56) References Cited

U.S. PATENT DOCUMENTS

2006/0123505 A1\* 6/2006 Kikuchi ............... C07K 14/415
800/278
2010/0196579 A1 8/2010 Ochiai et al.
2012/0309950 A1 12/2012 Ochiai

FOREIGN PATENT DOCUMENTS

WO 2009/008466 1/2009
WO 2011/081135 7/2011

OTHER PUBLICATIONS

Conrad et al, Biosystems. 1983;16(2):101-11. Evidence that natural selection acts on silent mutation.*
Santos-Rosa et al., "The yeast lipin Smp2 couples phospholipid biosynthesis to nuclear membrane growth", *The EMBO Journal*, vol. 24, No. 11, pp. 1931-1941, 2005.
Carman et al., "Phosphatidic Acid Phosphatase, a Key Enzyme in the Regulation of Lipid Synthesis", *The Journal of Biological Chemistry*, vol. 284, No. 5, pp. 2593-2597, published online Sep. 23, 2008.
Han et al., "The *Saccharomyces cerevisiae* Lipin Homolog Is a Mg2+-dependent Phosphatidate Phosphatase Enzyme", *The Journal of Biological Chemistry*, vol. 281, No. 14, pp. 9210-9218, 2006.
Han et al., "The Cellular Functions of the Yeast Lipin Homolog Pah1p Are Dependent on Its Phosphatidate Phosphatase Activity", *The Journal of Biological Chemistry*, vol. 282, No. 51, pp. 37026-37035, 2007.
Carman et al., "Roles of phosphatidate phosphatase enzymes in lipid metabolism", *Trends in Biochemical Sciences*, vol. 31, No. 12, pp. 694-699, 2006.
Pillai et al., "Characterization of triacylglycerol biosynthesis in subcellular fractions of an oleaginous fungus, *Mortierella ramanniana* var. *angulispora*", *Biochimica et Biophysica Acta*, vol. 1393, pp. 128-136, 1998.
Carman, "Phosphatidate phosphatases and diacylglycerol pyrophosphate phosphatases in *Saccharomyces cerevisiae* and *Escherichia coli*", *Biochimica et Biophysica Acta*, vol. 1348, pp. 45-55, 1997.
O'Hara et al., "Control of Phospholipid Synthesis by Phosphorylation of the Yeast Lipin Pah1p/Smp2p Mg2+-dependent Phosphatidate Phosphatase", *The Journal of Biological Chemistry*, vol. 281, No. 45, pp. 34537-34548, 2006.
International Search Report for PCT/JP2012/069172, mailed Aug. 28, 2012, along with an English language translation.
Written Opinion of the ISA for PCT/JP2012/069172, mailed Aug. 28, 2012, along with an English language translation.

\* cited by examiner

*Primary Examiner* — Sheridan Swope
(74) *Attorney, Agent, or Firm* — Greenblum & Bernstein, P.L.C.

(57) ABSTRACT

The present invention provides a novel phosphatidic acid phosphatase gene. The object of the present invention can be solved by providing a nucleic acid comprising the nucleotide sequence set forth in SEQ ID NO: 1, SEQ ID NO: 4, or SEQ ID NO: 5; a protein comprising the amino acid sequence set forth in SEQ ID NO: 2; and mutants thereof.

9 Claims, 6 Drawing Sheets

```
              1401                                                                   1500
genome  CCGACACGACAACGAGGTGGTGGAGGCAGAGGACGAAGTGCATCGGGAATCGTTTCTGAGTAATGTCGGGGGCGCGGGTTCGAATCGGTCTCACGAGTCT
   CDS  CCGACACGACAACGAGGTGGTGGAGGCAGAGGACGAAGTGCATCGGGAATCGTTTCTGAGTAATGTCGGGGGCGCGGGTTCGAATCGGTCTCACGAGTCT 1501                                                                   1600
genome  TTGACGGGAGGAACGAGTCTGCAGGATCTGAGTAACAATCATCATGGGGCCAAGCTCAACAGCACGGCGGGGCTATGGCTTTGATCAGGCAGGCGTAATGGAG
   CDS  TTGACGGGAGGAACGAGTCTGCAGGATCTGAGTAACAATCATCATGGGGCCAAGCTCAACAGCACGGCGGGGCTATGGCTTTGATCAGGCAGGCGTAATGGAG 1601         1635
genome  GTGGTCAACGGAACGATGTATACTTGGGACCATGA
   CDS  GTGGTCAACGGAACGATGTATACTTGGGACCATGA
```

Figure 2

```
               1                                                                                    100
MaPAP2-2  ----------MFSSMRFKARTRSLFLSYVKDWGLVIVILAVFSYVDTLEPFHRQFSVQDMSIQHPYAKKETVPVWMALVLAFILPAVVIGLIALLKRRS-
LbPAP2    MAFFQPSHARTKVPAMSPTRRRKLVFSYAPDWYAMMTIALFFS-LDKVNGYRRVFSLEDTSLRHPYAVHERVPNIAEYLICFVSPLLIQPVINFFTVRS-
ScDPP1    ----------MNRVSFIKTPFNIGAKWRLEDVFLLIMILLNYPVYYQQPFERQFYINDLTISHPYATTERVNNNMLFVYSFVVPSLTILIIGSILADRR 101                                                                                  200
MaPAP2-2  --YTDFHNGVLGLFLTQALVLIVTDSIKIAVGRPRPDFLDRCLDLYDNQAAGTPLGPLSDPINMLSNSTICTRT--HLLRDGFKSFPSGHSSFSFGGLGY
LbPAP2    --WWDFHNGSLGLVLGLALTGSVTQFVKITVGRPRPDVIDRCQPPTG--SVDPTFG-------LSNWTICTQASEAILRDGFRSEPSGHSSMSFAGLGF
ScDPP1    HLIFILYTSLLGLSLAWFSTSFFTNEIKNWIGRLRPDFLDRCQPVEG-LPLDTLFT----------AKDVCTTKNHERLLDGFRTTPSGHSSESFAGLGY 201                                                                                  300
MaPAP2-2  LSMFLAGKLHLFDERGHIYKSVVVLAPLIVAALIATSRVDDYRHHWQDVTVGAFIGATFAIFSYRQYYPSLASSKSDCPFAPRIGKDEHLPAALLPHH--
LbPAP2    LSFYLAGKLHLFDSRGHTGKAWLALSPFAGASLVAISRTMDYRHHWQDVLVGSILGTVLAYFSYRQYYPSLESDLSHRPYSPRIKHDEEDGLPIHVRTGS
ScDPP1    LYFWLCGQLLTESPLMPLWRKMVAFLPLLGAALIALSRTQDYRHHFVDVILGSMLGYIMAHFFYRRIFPPIDDP---LPFKPLMDDSDVTLEEAVTHQR- 301                                              382
MaPAP2-2  --HIHRHDNEVVEAEDEVHRESFLSNVGGAGSNRSHESLTGGTSLQDLSNNHHGAKLNSTAGYGFDQQRNGGGQRNDVYLGP
LbPAP2    ESHAFAHHESRTNPFLNTQARDPERYTSFDHTDAEDFELDGTVPRPRSGSLEEIWKDDETHSRMGSPFVDPFATKTSTAL--
ScDPP1    ----------IP-DEELHPLSDEGM---------------------------------------------------------
```

Figure 3

```
              1                                                                                   100
MaPAP2.2  --------------------MFSSMRFKARTRSLFLSYVKDWGLVIVILAVFSYVDTLEPFHRQFSVQDMSIQHPY----------AKKETVPVWMAL
MaPAP1    MGCFARKTHTTPHPDTNTTAVNGHHNVYSMQTRPKFGQWLKCTWLDILTMAVMGALGLGVYMLRPVPNRSFAVTFADGEIVYPEFAYPLRKEIVPIWLAS 101                                                                                 200
MaPAP2.2  VLAFILPAVVIGLIALLKRRSYTDFHNGVLGLFLTQALVLIVTDSIKIAVGRPRPDFLDRCLDLYDNQAAGTPLGPLSDPINMLSNSTICTRTHLLRDGF
MaPAP1    FLAVVVPVLGILLMQIRVR-SFWDVNNAIVGLLYSLITAAVFQVFIKWLIGGLRPHFLEVCKPDTS-LATDAGYNRKGFQQQYFTREICTGDEKEINDSL
                                                          *

201                                                                                 300
MaPAP2.2  KSFPSGHSSFSFGGLGYLSMFLAGKLHLFDERG-HIYKSVVVLAPLIVAALIATSRVDDYRHHWQDVTVGAFIGATFAIFSYRQYYPSLASSKSDCPFAP
MaPAP1    ESFPSGHSTAAFAGFVFLYLYLNAKLKVFSNYHPAMWKLIVIYTPILGAVLIGGALTIDEFHNWYDVVAGAIIGSVMAFSSYRMTYAAIWDWR------
              *                                                    *

301                                                                   396
MaPAP2.2  RIGKDEHLPAALLPHHHIHRHDNEVVEAEDEVHRESFLSNVGGAGSNRSHESLTGGTSLQDLSNNHHGAKLNSTAGYGFDQQRNGGGQRNDVYLGP
MaPAP1    ------YN--------HIPLNRNAPFPFLRDSGDLVGAVFTRKAGWGDAAKVPERGNDWNNHHGQTPNANQDGYQASSSIPLRSVGGGQAQPENIV-
```

Figure 4
A.
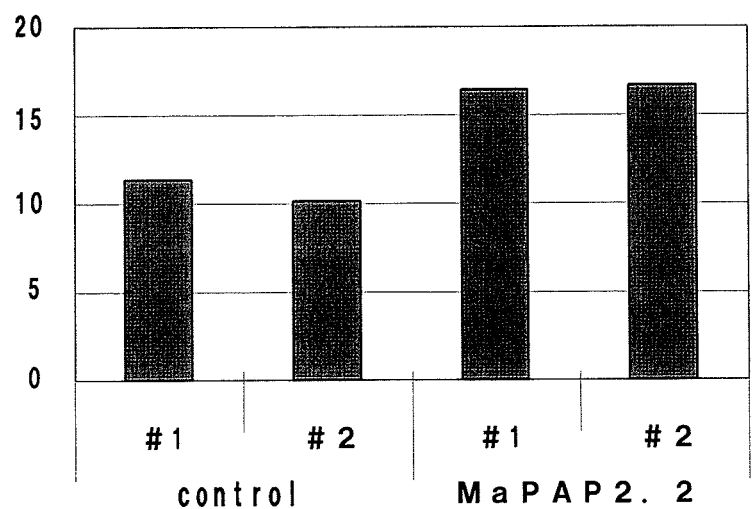
B.
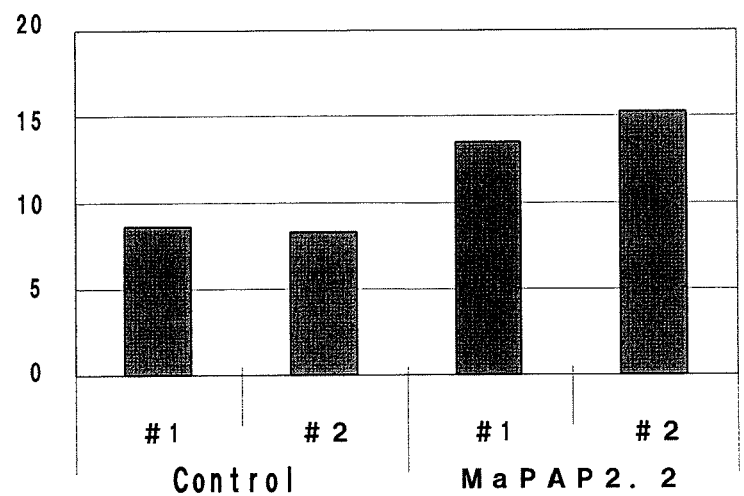

*Figure 5*
A.
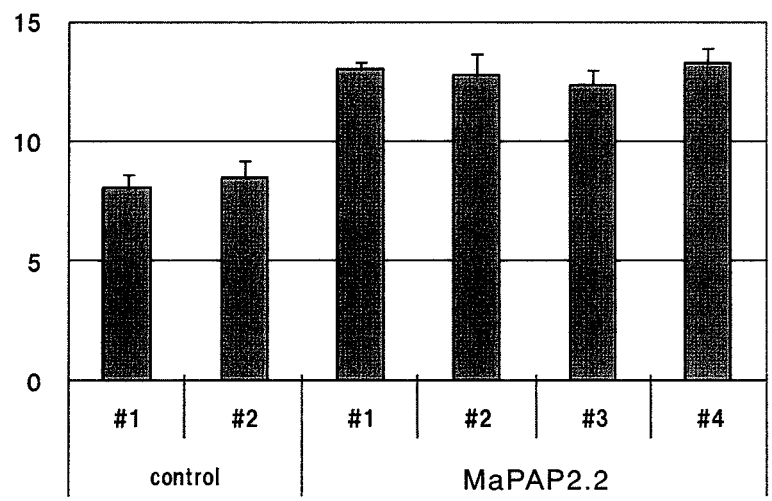
B.
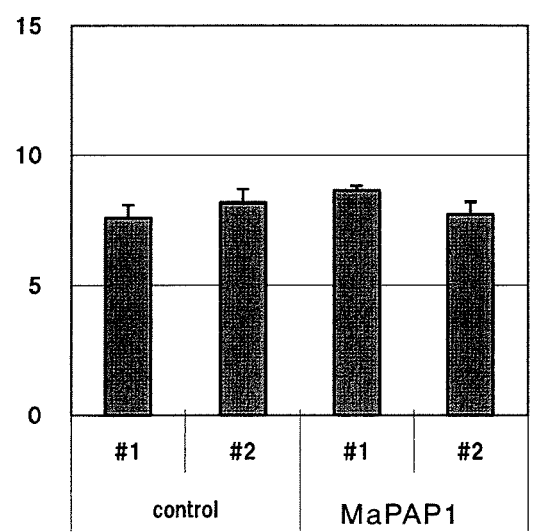

*Figure 6*
A.
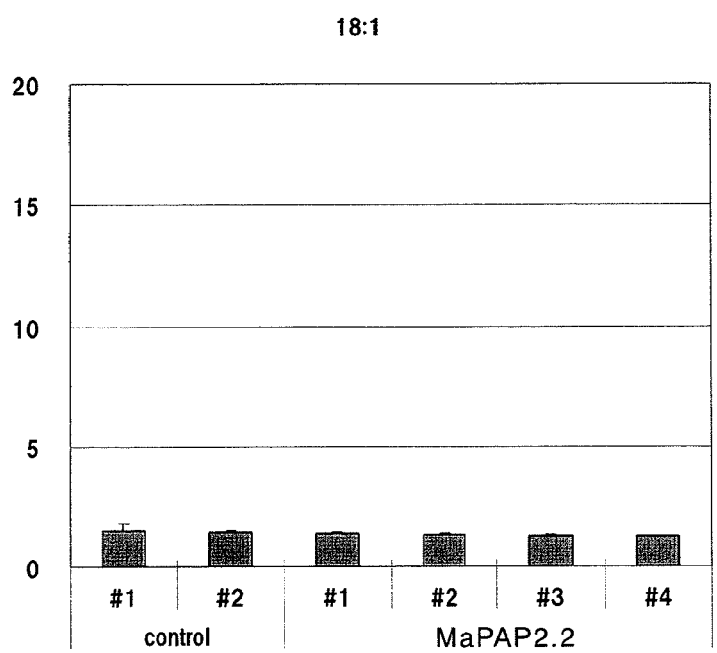
B.
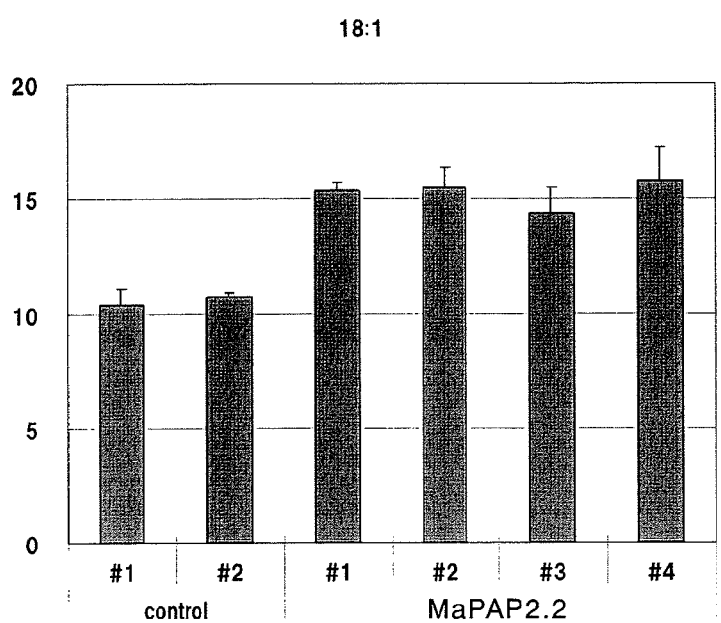

PHOSPHATIDIC ACID PHOSPHATASE GENE

SEQUENCE LISTING

The instant application contains a Sequence Listing which has been submitted electronically in ASCII format and is hereby incorporated by reference in its entirety. Said ASCII copy, created on Dec. 18, 2015, is named P45157_SL.txt and is 24,202 bytes in size.

TECHNICAL FIELD

The present application relates to a novel phosphatidic acid phosphatase gene and use thereof.

BACKGROUND ART

Fatty acids containing two or more unsaturated bonds are collectively referred to as polyunsaturated fatty acids (PUFAs) and are known to include arachidonic acid, dihomo-γ-linolenic acid, eicosapentaenoic acid, and docosahexaenoic acid. Some of the polyunsaturated fatty acids cannot be synthesized in the animal body, and such polyunsaturated fatty acids need to be ingested through food, as essential fatty acids. The polyunsaturated fatty acids are widely distributed. For example, arachidonic acid is isolated from lipids extracted from suprarenal glands or livers of animals. Polyunsaturated fatty acids, however, are contained in small amounts in animal organs, and the extraction and isolation of polyunsaturated fatty acids from the animal organs alone are insufficient to supply large amounts of polyunsaturated fatty acids. Microbial techniques have, therefore, been developed for obtaining polyunsaturated fatty acids through cultivation of various microorganisms. In particular, microorganisms of the genera *Mortierella* are known to produce lipids containing polyunsaturated fatty acids such as arachidonic acid.

Other attempts have also been made to produce polyunsaturated fatty acids in plants. Polyunsaturated fatty acids are known to form reserve lipids such as triacylglycerol (also referred to as triglyceride or TG) and accumulate in microorganism cells or plant seeds.

Triacylglycerol as a reserve lipid is produced in the organism as follows. An acyl group is introduced into glycerol-3-phosphate by glycerol-3-phosphate acyltransferase to generate lysophosphatidic acid, into which an acyl group is introduced by lysophosphate acyltransferase to generate phosphatidic acid. The phosphatidic acid is then dephosphorylated by phosphatidic acid phosphatase to generate diacylglycerol. An acyl group is introduced into the diacylglycerol by diacylglycerol acyltransferase to generate triacylglycerol.

In this pathway, phosphatidic acid (hereinafter also referred to as "PA" or 1,2-diacyl-sn-glycerol-3-phosphate) is a precursor of triacylglycerol as well as a biosynthetic precursor of diacyl glycerophospholipid. In cells such as yeast, phosphatidic acid cytidyltransferase acts on PA and cytidine 5'-triphosphate (CTP) to synthesize CDP diacylglycerol (CDP-DG), which is used for biosynthesis of various phospholipids.

As described above, dephosphorylation of PA for biosynthesis of diacylglycerol (hereinafter also referred to as "DG") is known to be catalyzed by phosphatidic acid phosphatase (E.C. 3.1.3.4, hereinafter also referred to as "PAP"). The PAP is known to be present in all organisms, from bacteria to vertebrates.

Yeast (*Saccharomyces cerevisiae*), which is a fungus, is known to have two types of PAPs (Non-Patent Documents 1, 2, and 7). One is a $Mg^{2+}$-dependent PAP (PAP1), and the other is a $Mg^{2+}$-independent PAP (PAP2). A PAH1 gene is known as a gene encoding PAP1 (Non-Patent Documents 3 to 5). A pah1Δ mutant also shows a PAP1 activity, which suggests the existence of other genes exhibiting the PAP1 activity. In the pah1Δ mutant, the nuclear membrane and the ER membrane are abnormally dilated, and the expression genes which plays a key role in biosynthesis of phospholipids is abnormally enhanced (Non-Patent Document 6).

On the other hand, known genes encoding PAP2 are DPP1 and LPP1 which exhibit most PAP2 activities in yeast. The enzymes encoded by these genes have broad substrate specificity and are known to act also on, for example, diacylglycerol pyrophosphate (DGPP), lysophosphatidic acid, sphingoid base phosphate, and isoprenoid phosphate to dephosphorylate them.

A lipid-producing fungus, *Mortierella alpina*, is known to have two types of genes, i.e., a MaPAH1.1 and a MaPAH1.2, as $Mg^{2+}$-dependent PAP1 homologs (Patent Document 1), and a MaPAP1 gene, which is a $Mg^{2+}$-independent PAP2 homolog (Patent Document 2).

CITATION LIST

Patent Documents

Patent Document 1: International Publication No. WO2011/081135
Patent Document 2: International Publication No. WO2009/008466

Non-Patent Documents

Non-Patent Document 1: Biochem. Biophys. Acta, 1348, 45-55, 1997
Non-Patent Document 2: Trends Biochem. Sci., 31(12), 694-699, 2006
Non-Patent Document 3: EMBO J., 24, 1931-1941, 2005
Non-Patent Document 4: J. Biol. Chem., 281(14), 9210-9218, 2006
Non-Patent Document 5: J. Biol. Chem., 281(45), 34537-34548, 2006
Non-Patent Document 6: J. Biol. Chem., 282(51), 37026-37035, 2007
Non-Patent Document 7: J. Biol. Chem., 284(5), 2593-2597, 2009

SUMMARY OF INVENTION

Technical Problem

Most of the PAP genes previously reported have not been investigated for their capability to vary the compositional ratio of fatty acids in the fatty acid compositions produced by the host cells in which the PAP genes are introduced and expressed. There is a demand to introduce a novel gene capable of producing fat with a desired compositional ratio of fatty acids or increasing the content of a desired fatty acid by being introduced into or expressed in a host cell.

It is an object of the present invention to provide a novel phosphatidic acid phosphatase gene, a protein encoded thereby, and methods of use thereof.

Solution to Problem

The present inventors have made intensive studies to solve the above-mentioned problems. The genome of lipid-producing fungus, *Mortierella alpina*, was analyzed to extract sequences having homology to known $Mg^{2+}$-independent phosphatidic acid phosphatase (PAP2) genes. The full-length cDNA was cloned through cDNA library screening or PCR to obtain the entire open reading frame (ORF) encoding PAP. The gene was then introduced into highly proliferative host cells (e.g. yeast cells) to confirm that the protein encoded by the cloned cDNA has a phosphatidic acid phosphatase activity. Thus, a gene related to a novel phosphatidic acid phosphatase (PAP) has been successfully cloned, leading to completion of the present invention. Accordingly, in one embodiment, the invention may be as follows.

(1) A nucleic acid according to any one of (a) to (g) below:

(a) a nucleic acid comprising a nucleotide sequence encoding a protein that consists of an amino acid sequence with deletion, substitution or addition of one or more amino acids in the amino acid sequence set forth in SEQ ID NO: 2 and that has a phosphatidic acid phosphatase activity;

(b) a nucleic acid comprising a nucleotide sequence that is hybridizable under stringent conditions with a nucleic acid consisting of a nucleotide sequence complementary to the nucleotide sequence set forth in SEQ ID NO: 1 and that encodes a protein having a phosphatidic acid phosphatase activity;

(c) a nucleic acid comprising a nucleotide sequence that has an identity of 70% or more with the nucleotide sequence set forth in SEQ ID NO: 1 and that encodes a protein having a phosphatidic acid phosphatase activity;

(d) a nucleic acid comprising a nucleotide sequence encoding a protein that consists of an amino acid sequence having an identity of 70% or more with the amino acid sequence set forth in SEQ ID NO: 2 and that has a phosphatidic acid phosphatase activity;

(e) a nucleic acid comprising a nucleotide sequence that is hybridizable under stringent conditions with a nucleic acid consisting of a nucleotide sequence complementary to a nucleotide sequence encoding a protein consisting of the amino acid sequence set forth in SEQ ID NO: 2 and that encodes a protein having a phosphatidic acid phosphatase activity;

(f) a nucleic acid comprising a nucleotide sequence that is hybridizable under stringent conditions with a nucleic acid consisting of a nucleotide sequence complementary to the nucleotide sequence set forth in SEQ ID NO: 4 and that includes an exon encoding a protein having a phosphatidic acid phosphatase activity; and (g) a nucleic acid comprising a nucleotide sequence that has an identity of 70% or more with the nucleotide sequence set forth in SEQ ID NO: 4 and that includes an exon encoding a protein having a phosphatidic acid phosphatase activity.

(2) A nucleic acid according to any one of (a) to (g) below:

(a) a nucleic acid comprising a nucleotide sequence encoding a protein that consists of an amino acid sequence with deletion, substitution, or addition of 1 to 110 amino acids in the amino acid sequence set forth in SEQ ID NO: 2 and has a phosphatidic acid phosphatase activity;

(b) a nucleic acid comprising a nucleotide sequence that is hybridizable with a nucleic acid consisting of a nucleotide sequence complementary to the nucleotide sequence set forth in SEQ ID NO: 1 under conditions of 2×SSC at 50° C. and encodes a protein having a phosphatidic acid phosphatase activity;

(c) a nucleic acid comprising a nucleotide sequence that has an identity of 90% or more with the nucleotide sequence set forth in SEQ ID NO: 1 and encodes a protein having a phosphatidic acid phosphatase activity;

(d) a nucleic acid comprising a nucleotide sequence encoding a protein that consists of an amino acid sequence having an identity of 90% or more with the amino acid sequence set forth in SEQ ID NO: 2 and has a phosphatidic acid phosphatase activity;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2 under conditions of 2×SSC at 50° C. and encodes a protein having a phosphatidic acid phosphatase activity;

(f) a nucleic acid comprising a nucleotide sequence that is hybridizable with a nucleic acid consisting of a nucleotide sequence complementary to the nucleotide sequence set forth in SEQ ID NO: 4 under conditions of 2×SSC at 50° C. and includes an exon encoding a protein having a phosphatidic acid phosphatase activity; and (g) a nucleic acid comprising a nucleotide sequence that has an identity of 90% or more with the nucleotide sequence set forth in SEQ ID NO: 4 and includes an exon encoding a protein having a phosphatidic acid phosphatase activity.

(3) A nucleic acid according to any one of (a) to (d) below:

(a) a nucleic acid comprising the nucleotide sequence set forth in SEQ ID NO: 1 or a fragment thereof;

(b) a nucleic acid comprising a nucleotide sequence encoding a protein consisting of the amino acid sequence set forth in SEQ ID NO: 2 or a fragment thereof;

(c) a nucleic acid comprising the nucleotide sequence set forth in SEQ ID NO: 4 or a fragment thereof; and (d) a nucleic acid comprising the nucleotide sequence set forth in SEQ ID NO: 5 or a fragment thereof.

(4) A nucleic acid according to (1) or (2), characterized in that the phosphatidic acid phosphatase activity has a higher substrate specificity for a $C_{18}$ acyl group-containing phosphatidic acid than for a $C_{17}$ acyl group-containing one.

(5) A protein according to (a) or (b) below:

(a) a protein comprising an amino acid sequence with deletion, substitution, or addition of one or more amino acids in SEQ ID NO: 2 and having a phosphatidic acid phosphatase activity, and (b) a protein comprising an amino acid sequence that has an identity of 70% or more with the amino acid sequence set forth in SEQ ID NO: 2 and having a phosphatidic acid phosphatase activity.

(6) A protein according to (a) or (b) below:

(a) a protein comprising an amino acid sequence with deletion, substitution, or addition of 1 to 110 amino acids in the amino acids in SEQ ID NO: 2 and having a phosphatidic acid phosphatase activity; and (b) a protein comprising an amino acid sequence that has an identity of 90% or more with the amino acid sequence set forth in SEQ ID NO: 2, and having a phosphatidic acid phosphatase activity.

(7) A nucleic acid according to (5) or (6), characterized in that the phosphatidic acid phosphatase activity has a higher substrate specificity for a $C_{18}$ acyl group-containing phosphatidic acid than for a $C_{17}$ acyl group-containing one.

(8) A protein consisting of the amino acid sequence set forth in SEQ ID NO: 2.

(9) A recombinant vector comprising a nucleic acid according to any one of (1) to (4).

(10) A transformant transformed with the recombinant vector according to (9).

Advantageous Effects of Invention

The present invention provides a novel PAP gene, a protein encoded thereby, and methods of use thereof. The PAP of the present invention is expected to produce fatty acids in a host cell, the fatty acids having a compositional ratio different from that of fatty acids produced in a host cell into which PAP is not introduced. This can provide lipids having desired characteristics and effects and is therefore useful in application to, for example, foods, cosmetics, pharmaceuticals, and soap.

BRIEF DESCRIPTION OF DRAWINGS

FIG. 1-1 shows a genomic sequence (nucleotides 1-1,400 of SEQ ID NO: 4) and a CDS nucleotide sequence of MaPAP2.2 (nucleotides 1-857 of SEQ ID NO: 3).

FIG. 1-2 is a continuation of FIG. 1-1 (nucleotides 1,401-1,635 of SEQ ID NO: 4 and nucleotides 858-1,092 of SEQ ID NO: 3, respectively, in order of appearance).

FIG. 2 shows an alignment of an amino acid sequence of MaPAP2.2 (SEQ ID NO: 2) and amino acid sequences of a putative protein derived from *Laccaria bicolor* (SEQ ID NO: 10) and ScDPP1 (YDR284C: accession number AAS56070) derived from yeast (SEQ ID NO: 11).

FIG. 3 shows an alignment of amino acid sequences of MaPAP2.2 (SEQ ID NO: 2) and MaPAP1 (SEQ ID NO: 12) known as a $Mg^{2+}$-independent PAP (PAP2) derived from *Mortierella alpina* (WO2009/008466). The three double-underlined segments represent conserved regions among $Mg^{2+}$-independent phosphatidic acid phosphatase type 2 (PAP2) family enzymes (domains 1, 2, and 3 in order from the terminal N) and "*" represents an amino acid residue essential for the PAP activity.

FIG. 4 shows graphs illustrating the results of investigation on $Mg^{2+}$-dependence of the activity that converts 18:2-PA to 18:2-DG of MaPAP2.2 (n=1). Graph A shows the result of the addition of $Mg^{2+}$. Graph B shows the results of the addition of EDTA ($Mg^{2+}$-free). The vertical axes show the amounts of 18:2-DG (found in DG fractions) per protein (μg/mg·protein) in crude enzyme solutions. The results were obtained with reaction solutions containing the supernatant of the cell homogenate of yeast transformed with plasmid pYE22m containing no MaPAP2.2 gene (control (#1 and #2)) and plasmid pYE-MaPAP2.2 containing the MaPAP2.2 gene (#1 and #2).

FIG. 5 shows graphs illustrating the results of investigation on the activity of MaPAP2.2 (A) and MaPAP1 (B) that converts 18:2-PA to 18:2-DG (n=3) in the $Mg^{2+}$-free reaction solution. The vertical axes show the amounts of 18:2-DG (found in DG fractions) per protein (μg/mg·protein) in crude enzyme solutions. The results were obtained with reaction solutions containing the supernatant of the cell homogenate of yeast transformed with plasmid pYE22m containing no MaPAP2.2 gene (control (#1 and #2)), plasmid pYE-MaPAP2.2 containing the MaPAP2.2 gene (#1, #2, #3, and #4,), and plasmid pYE-MaPAP1 containing the MaPAP1 gene (#1 and #2).

FIG. 6A shows graphs illustrating the results of investigation on the amount of 18:1-DG without the addition of phosphatidic acid as a substrate in the reaction solutions containing the MaPAP2.2 and the controls (n=3). FIG. 6B shows graphs illustrating the results of investigation on the amount of 18:1-DG with the addition of 18:1-PA as a substrate in the reaction solutions containing the MaPAP2.2 and the controls (n=3). Each vertical axis shows the amount of 18:1-DG (found in DG fractions) per protein (μg/mg·protein) in a crude enzyme solution. The results were obtained with reaction solutions containing the supernatant of the cell homogenate of yeast transformed with plasmid pYE22m containing no MaPAP2.2 gene (control (#1 and #2)) and plasmid pYE-MaPAP2.2 containing the MaPAP2.2 gene (#1, #2, #3, and #4).

DESCRIPTION OF EMBODIMENTS

Figure 7:
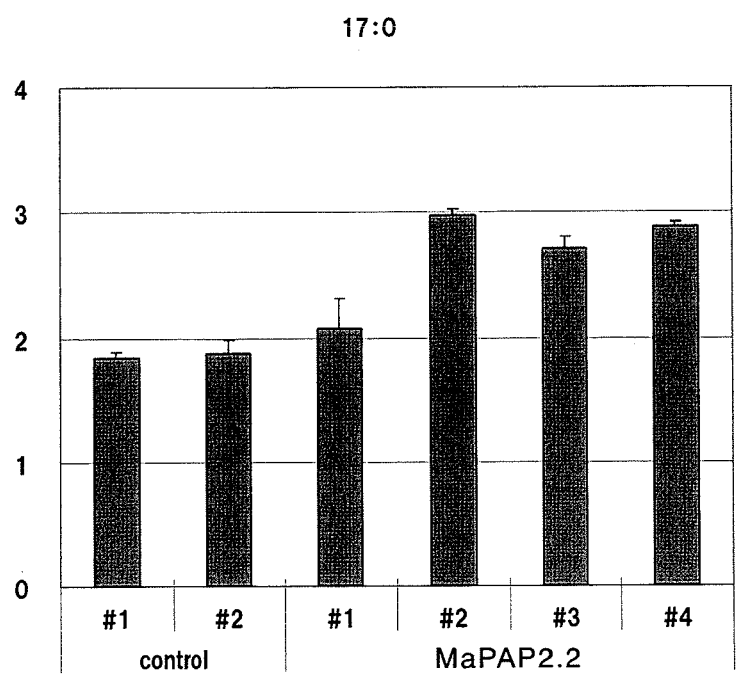
FIG. 7 shows graphs illustrating the results of investigation on the amount of 17:0-DG with the addition of 17:0-PA as a substrate in the reaction solutions containing the MaPAP2.2 and the controls (n=3). The vertical axes show the amounts of 17:0-DG (found in DG fractions) per protein (μg/mg·protein) in crude enzyme solutions. The results were obtained with reaction solutions containing the supernatant of the cell homogenate of yeast transformed with plasmid pYE22m containing no MaPAP2.2 gene (control (#1 and #2)) and plasmid pYE-MaPAP2.2 containing the MaPAP2.2 gene (#1, #2, #3, and #4).

The present invention relates to a novel phosphatidic acid phosphatase gene derived from the genus *Mortierella*, wherein the phosphatidic acid phosphatase dephosphorylates phosphatidic acid to produce diacylglycerol, a protein encoded thereby, and methods of use thereof.

The phosphatidic acid phosphatase is an enzyme that catalyzes a reaction of generating diacylglycerol by dephosphorylation of phosphatidic acid. The substrate of PAP of the present invention is usually phosphatidic acid, but is not limited thereto.

Nucleic Acid Encoding Phosphatidic Acid Phosphatase

Phosphatidic acid phosphatase (PAP) of the present invention includes MaPAP2.2 and mutants thereof. The correspondence between cDNA, CDS, ORF, which are nucleic acids encoding MaPAP2.2, and an amino acid sequence of MaPAP2.2 are summarized in Table 1.

TABLE 1

| | MaPAP2.2 | |
|---|---|---|
| | SEQ ID NO | Corresponding region in SEQ ID NO: 5 |
| cDNA | SEQ ID NO: 5 | ***** |
| CDS | SEQ ID NO: 3 | Positions 75 to 1166 |
| ORF | SEQ ID NO: 1 | Positions 75 to 1163 |
| Amino acid sequence | SEQ ID NO: 2 | ***** |

Namely, sequences related to MaPAP2.2 include SEQ ID NO: 2 showing the amino acid sequence of MaPAP2.2; SEQ ID NO: 1 showing the sequence of the ORF region of MaPAP2.2; SEQ ID NO: 3 showing the sequence of the CDS region of MaPAP2.2; and SEQ ID NO: 5 showing the sequence of the cDNA of MaPAP2.2. Among these sequences, SEQ ID NO: 1 corresponds to the nucleotides 75 to 1163 in the sequence set forth in SEQ ID NO: 5; and SEQ ID NO: 3 corresponds to the nucleotides 75 to 1166 in the sequence set forth in SEQ ID NO: 5. SEQ ID NO: 4 shows a genomic nucleotide sequence encoding MaPAP2.2. The genomic sequence set forth in SEQ ID NO: 4 is composed of three exons and two introns, and the exon regions correspond to the nucleotides 1 to 207, 445 to 582, and 889 to 1632 in SEQ ID NO: 4.

The nucleic acids of the present invention includes single-stranded and double-stranded DNAs and their complementary RNAs, which may be either naturally occurring or artificially prepared. Examples of DNA include, but not limited to, genomic DNAs, cDNAs corresponding to the genomic DNAs, chemically synthesized DNAs, PCR-amplified DNAs, combinations thereof, and DNA/RNA hybrids.

Preferred embodiments for the nucleic acids of the present invention include those containing (a) the nucleotide sequence set forth in SEQ ID NO: 1, (b) a nucleotide sequence encoding a protein consisting of the amino acid sequence set forth in SEQ ID NO: 2, and (c) the nucleotide sequence set forth in SEQ ID NO: 5.

In order to obtain these nucleotide sequences, nucleotide sequence data of ESTs or genomic DNAs from organisms having PAP activity may be used to search for a nucleotide sequence encoding a protein having a homology with known proteins having PAP activity. Preferred organisms having PAP activity are lipid-producing fungi including, but not limited to, M. alpina.

For EST analysis, a cDNA library is first prepared. The cDNA library may be prepared with reference to "Molecular Cloning, A Laboratory Manual, 3rd ed." (Cold Spring Harbor Press (2001)). Alternatively, a commercially available cDNA library preparation kit may be used. A cDNA library suitable for the present invention can be prepared, for example, by the following procedure. That is, an appropriate strain of M. alpina, a lipid-producing fungus, is inoculated into an appropriate medium and is pre-cultured for an appropriate period. Among culture conditions suitable for this pre-culture are, for example, a medium composition containing 1.8% glucose and 1% yeast extract, a pH of 6.0, a culture period of 3 to 4 days, and a culture temperature of 28° C. The pre-cultured product is then subjected to main culture under appropriate conditions. A medium composition suitable for the main culture contains, for example, 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, and 0.05% $MgCl_2.6H_2O$, and has a pH of 6.0. Culture conditions suitable for the main culture involve, for example, aeration and agitation culture at 300 rpm, 1 vvm, and 26° C. for 8 days. An appropriate amount of glucose may be added during the culture. The cultures are sampled at appropriate time points during the main culture, from which the cells are collected to prepare total RNA. The total RNA can be prepared by any known method such as a guanidine hydrochloride/CsCl procedure. Poly(A)+RNA can be purified from the resulting total RNA with a commercially available kit, and a cDNA library can be constructed with a commercially available kit. The nucleotide sequence of any clone from the prepared cDNA library is determined using primers that are designed on a vector to allow determination of the nucleotide sequence of an insert. As a result, ESTs can be obtained. For example, preparation of a cDNA library using a ZAP cDNA GigapackIII Gold Cloning Kit (STRATAGENE) enables directional cloning.

In analysis of genomic DNA, cells of an organism having PAP activity are cultured, from which the genomic DNA is then prepared. The nucleotide sequence of the resulting genomic DNA is determined, and the determined nucleotide sequence is assembled. The finally obtained supercontig sequences are searched for a sequence encoding an amino acid sequence having a high homology with the amino acid sequence of a known protein having PAP activity. Primers are prepared from the supercontig sequences identified as that encoding such an amino acid sequence. PCR is then performed using the cDNA library as a template, and the resulting DNA fragment is inserted into a plasmid for cloning. The cloned plasmid as a template and the above-mentioned primers are used for PCR to prepare a probe, which is then used to screen the cDNA library.

A homology search for the amino acid sequences of MaPAP2.2 was performed against amino acid sequences registered in GenBank with BLASTp program. The resulting amino acid sequence gave a hit with the highest score to a deduced protein of Laccaria bicolor (SEQ ID NO: 10, accession Number: XP_001878243) to share a nucleotide sequence identity of 36.7%. The identity between the amino acid sequence of MaPAP1, which is a known PAP2 ($Mg^{2+}$-independent PAP) derived from Mortierella alpina, and the amino acid sequence of MaPAP2.2 was 20.5%.

The present invention also includes nucleic acids functionally equivalent to a nucleic acid including the above nucleotide sequence set forth in SEQ ID NO: 1 or a nucleotide sequence encoding a protein consisting of the amino acid sequence set forth in SEQ ID NO: 2. The phrase "functionally equivalent" is intended to mean that a protein encoded by the nucleotide sequence of the present invention and a protein consisting of the amino acid sequence of the present invention have a phosphatidic acid phosphatase (PAP) activity. As used herein, "PAP activity" refers to an activity of catalyzing the reaction of dephosphorylating phosphatidic acid to produce a diacylglycerol. The PAP activity may have, but not limited to, a higher substrate specificity for a $C_{18}$ acyl group-containing phosphatidic acid than for a $C_{17}$ acyl group-containing one. Furthermore, the PAP activity may be, but not limited to, independent of $Mg^{2+}$.

Such nucleic acids that are mutants of the nucleic acids comprising the nucleotide sequence set forth in SEQ ID NO: 1 or a nucleic acid comprising a nucleotide sequence encoding a protein consisting of the amino acid sequence set forth in SEQ ID NO: 2, and that are functionally equivalent to the nucleic acids include nucleic acids comprising nucleotide sequences shown in any one of (a) to (g) below.

(a) A nucleic acid comprising a nucleotide sequence encoding a protein that consists of an amino acid sequence with deletion, substitution, or addition of one or more amino acids in the amino acid sequence set forth in SEQ ID NO: 2 and that has PAP activity Examples of the nucleotide sequence contained in the nucleic acid of the present invention include nucleotide sequences encoding a protein that consists of an amino acid sequence with deletion, substitution, or addition of one or more amino acids in the amino acid sequence set forth in SEQ ID NO: 2 and that has the PAP activity.

Specifically, the nucleotide sequence contained in the nucleic acid of the present invention is a nucleotide sequence encoding a protein having PAP activity and consisting of:

(i) an amino acid sequence with deletion of one or more (preferably one or several (e.g., 1 to 110, 1 to 100, 1 to 75, 1 to 50, 1 to 30, 1 to 25, 1 to 20, or 1 to 15, more preferably 10, 9, 8, 7, 6, 5, 4, 3, 2, or 1)) amino acids in the amino acid sequence set forth in SEQ ID NO: 2;

(ii) an amino acid sequence having substitution of one or more (preferably one or several (e.g., 1 to 110, 1 to 100, 1 to 75, 1 to 50, 1 to 30, 1 to 25, 1 to 20, or 1 to 15, more preferably 10, 9, 8, 7, 6, 5, 4, 3, 2, or 1)) other amino acids in the amino acid sequence set forth in SEQ ID NO: 2;

(iii) an amino acid sequence having addition of one or more (preferably one or several (e.g., 1 to 110, 1 to 100, 1 to 75, 1 to 50, 1 to 30, 1 to 25, 1 to 20, or 1 to 15, more preferably 10, 9, 8, 7, 6, 5, 4, 3, 2, or 1)) other amino acids to the amino acid sequence set forth in SEQ ID NO: 2; or (iv) an amino acid sequence in any combination of (i) to (iii).

Among them, the substitution is preferably conservative substitution, which means replacement of a specific amino acid residue by another residue having similar physicochemical characteristics, and may be any substitution that does not substantially affect the structural characteristics of the original sequence. For example, any substitution is available as long as the substituted amino acids do not disrupt the helix of the original sequence or do not disrupt any other secondary structure characterizing the original sequence.

Conservative substitution is generally introduced by synthesis with a biological system or chemical peptide synthesis, preferably by chemical peptide synthesis. In such a case, substituents may include an nonnatural amino acid residue, a peptidomimetic, or a reversed or inverted form where an unsubstituted region is reversed or inverted in the amino acid sequence.

Unlimited examples of the mutually substitutable amino acid residues are classified and listed below:

Group A: leucine, isoleucine, norleucine, valine, norvaline, alanine, 2-aminobutanoic acid, methionine, O-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine and tyrosine.

In non-conservative substitution, a member of one of these groups can be replaced by a member from another group. In such a case, in order to maintain the biological functions of the protein of the present invention, the hydropathic indices of amino acids (hydropathic amino acid indices) (Kyte, et al., J. Mol. Biol., 157: 105-131 (1982)) are preferably considered.

For the non-conservative substitution, amino acid substitution can be accomplished on the basis of hydrophilicity.

Throughout the specification and drawings, nucleotides, amino acids, and abbreviations thereof are those according to the IUPAC-IUB Commission on Biochemical Nomenclature or those conventionally used in the art, for example, as described in Immunology—A Synthesis (second edition, edited by E. S. Golub and D. R. Gren, Sinauer Associates, Sunderland, Mass. (1991)). Moreover, amino acids which may have optical isomers are intended to represent their L-isomers, unless otherwise specified.

Stereoisomers, such as D-amino acids of the above-mentioned amino acids, nonnatural amino acids, such as α,α-disubstituted amino acids, N-alkylamino acids, lactic acid, and other unconventional amino acids can also be members forming the proteins of the present invention.

Note that in the protein notation used herein, the left-hand direction is the amino terminal direction and the right-hand direction is the carboxy terminal direction, in accordance with standard usage and convention in the art.

Similarly, in general, unless otherwise specified, the left-hand end of a single-stranded polynucleotide sequence is the 5'-end and the left-hand direction of double-stranded polynucleotide sequence is referred to as the 5'-direction.

Those skilled in the art can design and prepare appropriate mutants of the proteins described herein using methods known in the art. Thus, for example, they can identify suitable regions in the protein molecule whose structure can be modified without impairing the biological activity of the protein of the present invention through targeting regions believed to be less important for the biological activity of the protein. Those skilled in the art also can identify residues and regions of the molecules that are conserved among similar proteins, and also can introduce conservative amino acid substitution into regions that may be important for the biological activity or structure of the protein of the present invention, without impairing the biological activity and without adversely affecting the polypeptide structure of the protein.

Particularly, as is double underlined in FIG. 3, the amino acid sequence (SEQ ID NO: 2) of MaPAP2.2 contains three conserved regions in $Mg^{2+}$-independent phosphatidic acid phosphatase 2 (PAP2) family enzymes at residues 115-123, 172-175 and 229-233. In these three conserved regions in PAP2 family enzymes, arginine in domain 1 and histidine in domains 2 and 3 are known as amino acids essential for activity, and the amino acids are also conserved in MaPAP2.2 as arginine at residue 122 and histidine at residues 175 and 229 of SEQ ID NO: 2. The above conserved regions are essential for PAP2 family enzymes and are also important for the PAP of the present invention. Thus, mutants according to the present invention may contain the above conserved regions.

Those skilled in the art can conduct a so-called structure-function study, which identifies residues of a peptide that is important for a biological activity or structure of a protein of the present invention and is similar to a peptide of the protein, compares the amino acid residues between these two peptides, and thereby predicts which residue in the protein similar to the protein of the present invention is the amino acid residue corresponding to the important amino acid residue for the biological activity or structure. They also can select a mutant that retains the biological activity of the protein of the present invention by selecting an amino acid substituent chemically similar to the predicted amino acid residue. Likewise, those skilled in the art can analyze the three-dimensional structure and amino acid sequence of this protein mutant. The analytical results can further be used to predict the alignment of amino acid residues involved in the three-dimensional structure of the protein. On the basis of the analytical results as mentioned above, those skilled in the art can prepare a mutant that causes no change in these amino acid residues predicted to be on the protein surface, which may be involved in important interactions with other molecules. Those skilled in the art can also prepare a mutant having single amino acid substitution for any of the amino acid residues which form the protein of the present invention. These mutants can be screened by any known assay to collect information about the individual mutants, which allows the evaluation of the usefulness of individual amino acid residues forming the protein of the present invention on the basis of comparison of biological activity in the following case: a mutant having substitution of a specific amino acid residue shows a lower biological activity than that of the protein of the present invention; such a mutant shows no biological activity; or such a mutant produces unsuitable activity to inhibit the biological activity of the protein of the present invention. Moreover, those skilled in the art can readily analyze amino acid substitution undesirable for mutants of the protein of the present invention based on information collected from such routine experiments alone or in combination with other mutations.

As described above, a protein consisting of an amino acid sequence with deletion, substitution, or addition of one or more amino acids in the amino acid sequence set forth in SEQ ID NO: 2 can be prepared according to methods, such as site-directed mutagenesis as described in, for example, "Molecular Cloning, A Laboratory Manual 3rd ed." (Cold Spring Harbor Press (2001)); "Current Protocols in Molecular Biology" (John Wiley & Sons (1987-1997); Kunkel, (1985), Proc. Natl. Acad. Sci. USA, 82: 488-92; or Kunkel, (1988), Method Enzymol., 85: 2763-6). Preparation of a mutant with such a mutation including amino acid deletion, substitution, or addition may be accomplished, for example, by known procedures such as a Kunkel method or a Gapped duplex method using a mutation-introducing kit based on site-directed mutagenesis such as a QuikChange™ Site-Directed Mutagenesis Kit (manufactured by Stratagene), a GeneTailor™ Site-Directed Mutagenesis System (manufactured by Invitrogen), or a TaKaRa Site-Directed Mutagenesis System (e.g., Mutan-K, Mutan-Super Express Kin; manufactured by Takara Bio Inc.).

Methods of introducing deletion, substitution, or addition of one or more amino acids into the amino acid sequence of a protein while retaining its activity include, besides site-directed mutagenesis mentioned above, a method of treating a gene with a mutagen and a method of selectively cleaving a gene for deletion, substitution, or addition of a selected nucleotide and then ligating the segments.

The nucleotide sequence contained in the nucleic acid of the present invention is preferably a nucleotide sequence encoding a protein that consists of an amino acid sequence with deletion, substitution, or addition of 1 to 30, 1 to 20, or 1 to 10 amino acids in the amino acid sequence set forth in SEQ ID NO: 2 and that has PAP activity.

The number and sites of amino acid mutations or modifications in the protein which is encoded by the nucleic acid of the present invention are not limited as long as PAP activity is retained.

PAP activity can be determined by a known method, for example, see J. Biol. Chem., 273, 14331-14338 (1998).

For example, PAP activity may be measured as follows: A crude enzyme solution is prepared by disrupting transformed cells expressing the PAP of the present invention, centrifugating the cell homogenate, and collecting the supernatant. The resulting crude enzyme solution may be further subjected to purification of the PAP of the present invention. The crude enzyme solution containing the PAP of the present invention or the purified PAP of the present invention is added to a reaction solution containing 100 μg/mL phosphatidic acid, and 50 mM Tris-HCl (pH 7.5), followed by reaction at 25° C. to 28° C. for an appropriate time. The reaction is terminated by addition of a mixture of chloroform and methanol, and lipids are then extracted. The resulting lipids are fractionated by thin layer chromatography to determine the amount of produced diacylglycerol.

(b) A nucleic acid comprising a nucleotide sequence that is hybridizable under stringent conditions with a nucleic acid consisting of a nucleotide sequence complementary to the nucleotide sequence set forth in SEQ ID NO: 1 and that encodes a protein having PAP activity Examples of the nucleotide sequence contained in the nucleic acid of the present invention include nucleotide sequences that are hybridizable under stringent conditions with a nucleic acid consisting of a nucleotide sequence complementary to the nucleotide sequence set forth in SEQ ID NO: 1 and that encode a protein having PAP activity.

Such a nucleotide sequence can be prepared by a method known to those skilled in the art from, for example, a cDNA library or a genomic library by a known hybridization process, such as colony hybridization, plaque hybridization, or Southern blotting using a probe which is produced by a method known to those skilled in the art by using an appropriate fragment.

Detailed procedure of the hybridization can be found in "Molecular Cloning, A Laboratory Manual 3rd ed." (Cold Spring Harbor Press (2001), in particular, Sections 6 and 7), "Current Protocols in Molecular Biology" (John Wiley & Sons (1987-1997), in particular, Sections 6.3 and 6.4), and "DNA Cloning 1: Core Techniques, A Practical Approach 2nd ed." (Oxford University (1995), in particular, Section 2.10 for hybridization conditions).

The stringency of hybridization is determined primarily based on hybridization conditions, more preferably based on hybridization conditions and washing conditions. The term "stringent conditions" used herein is intended to include moderately or highly stringent conditions.

Specifically, examples of the moderately stringent conditions include hybridization conditions of 1×SSC to 6×SSC at 42° C. to 55° C., more preferably 1×SSC to 3×SSC at 45° C. to 50° C., and most preferably 2×SSC at 50° C. In the case of a hybridization solution containing, for example, about 50% formamide, a hybridization temperature of lower than the above-mentioned temperature by 5° C. to 15° C. may be employed. Washing conditions are, for example, 0.5×SSC to 6×SSC at 40° C. to 60° C. Usually 0.05% to 0.2% SDS, preferably about 0.1% SDS may be added to the hybridization solution and washing solution.

Highly stringent (high stringent) conditions include hybridization and/or washing at higher temperature and/or lower salt concentration, compared to the moderately stringent conditions. Examples of the hybridization conditions include 0.1×SSC to 2×SSC at 55° C. to 65° C., more preferably 0.1×SSC to 1×SSC at 60° C. to 65° C., and most preferably 0.2×SSC at 63° C. Washing conditions are, for example, 0.2×SSC to 2×SSC at 50° C. to 68° C., and more preferably 0.2×SSC at 60° C. to 65° C.

Examples of the hybridization conditions particularly used in the present invention include, but not limited to, prehybridization in 5×SSC, 1% SDS, 50 mM Tris-HCl (pH 7.5) and 50% formamide at 42° C., followed by hybridization with a probe overnight at 42° C., and then washing three times in 0.2×SSC, 0.1% SDS at 65° C. each for 20 minutes.

Commercially available hybridization kits including no radioactive probe can also be used. Specifically, for example, a DIG nucleic acid detection kit (Roche Diagnostics) or an ECL direct labeling & detection system (manufactured by Amersham) is used for hybridization.

Preferred examples of the nucleotide sequence falling within the present invention include nucleotide sequences that are hybridizable under conditions of 2×SSC at 50° C. with a nucleic acid consisting of a nucleotide sequence complementary to the nucleotide sequence set forth in SEQ ID NO: 1 and that encodes a protein having PAP activity.

(c) A nucleic acid comprising a nucleotide sequence that has an identity of 70% or more with the nucleotide sequence set forth in SEQ ID NO: 1 and that encodes a protein having PAP activity The nucleotide sequence contained in the nucleic acid of the present invention includes a nucleotide sequence that has an identity of at least 70% with the nucleotide sequence set forth in SEQ ID NO: 1 and that encodes a protein having PAP activity.

Preferably, for example, the nucleic acid comprises a nucleotide sequence having an identity of at least 75%, more preferably 80% or more (e.g., 85% or more, more preferably 90% or more, and most preferably 95%, 98%, or 99% or more) with the nucleotide sequence set forth in SEQ ID NO: 1 and encoding a protein having PAP activity.

The percent identity between two nucleotide sequences can be determined by visual inspection and mathematical calculation, but is preferably determined by comparing sequence information of two nucleic acids using a computer program. Computer programs for sequence comparison, include, for example, the BLASTN program (Altschul et al., (1990), J. Mol. Biol., 215: 403-10) version 2.2.7, available from the website of the National Library of Medicine: www.ncbi.nlm.nih.gov/blast/bl2seq/bls.html or the WU-BLAST 2.0 algorithm. Standard default parameter settings for WU-BLAST 2.0, which are described at the following Internet site: blast.wustl.edu, can be utilized.

(d) A nucleic acid comprising a nucleotide sequence encoding a protein that consists of an amino acid sequence having an identity of 70% or more with the amino acid sequence set forth in SEQ ID NO: 2 and that has PAP activity The nucleotide sequence contained in the nucleic acid of the present invention includes a nucleotide sequence encoding a protein that consists of an amino acid sequence having an identity of 70% or more with the amino acid sequence set forth in SEQ ID NO: 2 and that has PAP activity.

The protein encoded by the nucleic acid of the present invention may be any protein having an identity with the amino acid sequence of MaPAP2.2, as long as said protein has PAP activity. Specific examples of the amino acid sequence of the protein encoded by the nucleic acid of the present invention include an amino acid sequence having an identity of 75% or more, preferably 80% or more, more preferably 85% or more, and most preferably 90% or more (e.g., 95% or more, furthermore 98% or more) with the amino acid sequence set forth in SEQ ID NO: 2.

The nucleotide sequence contained in the nucleic acid of the present invention is preferably a nucleotide sequence consisting of an amino acid sequence having an identity of 90% or more with the amino acid sequence set forth in SEQ ID NO: 2 and encoding a protein having PAP activity, more preferably, a nucleotide sequence consisting of an amino acid sequence having an identity of 95% or more with the amino acid sequence set forth in SEQ ID NO: 2 and encoding a protein having PAP activity.

The percent identity between two amino acid sequences can be determined by visual inspection and mathematical calculation. Alternatively, the percent identity can be determined using a computer program. Examples of such a computer program include BLAST, FASTA (Altschul et al., J. Mol. Biol., 215: 403-410, (1990)) and ClustalW. In particular, various conditions (parameters) for an identity search with the BLAST program are described by Altschul et al. (Nucl. Acids. Res., 25, pp. 3389-3402, 1997) and publicly available via the website of the National Center for Biotechnology Information (NCBI) of USA or the DNA Data Bank of Japan (DDBJ) (BLAST Manual, Altschul et al., NCB/NLM/NIH Bethesda, Md. 20894; Altschul et al.). The percent identity can also be determined using genetic information processing programs, such as GENETYX Ver.7 (Genetyx), DNASIS Pro (Hitachisoft), and Vector NTI (Infomax).

A specific alignment scheme for aligning a plurality of amino acid sequences can also show the matching of sequences in a specific short region and can therefore detect a region having a very high sequence identity in such a short region even if the full-length sequences have no significant relationship therebetween. In addition, the BLAST algorithm can use the BLOSUM62 amino acid scoring matrix, and the following selection parameters can be used: (A) inclusion of filters to mask a segment of a query sequence having low compositional complexity (as determined by the SEG program of Wootton and Federhen (Computers and Chemistry, 1993); also see Wootton and Federhen, 1996, "Analysis of compositionally biased regions in sequence databases", Methods Enzymol., 266: 554-71) or to mask segments consisting of short-periodicity internal repeats (as determined by the XNU program of Claverie and States (Computers and Chemistry, 1993), and (B) a statistical significance threshold for reporting matches against database sequences, or the expected probability of matches being found merely by chance, according to the statistical model of E-score (Karlin and Altschul, 1990); if the statistical significance ascribed to a match is greater than this E-score threshold, the match will not be reported.

(e) A nucleic acid comprising a nucleotide sequence that is hybridizable under stringent conditions with a nucleic acid consisting of a nucleotide sequence complementary to a nucleotide sequence encoding a protein consisting of the amino acid sequence set forth in SEQ ID NO: 2 and that encodes a protein having PAP activity The nucleotide sequence contained in the nucleic acid of the present invention includes a nucleotide sequence that is hybridizable under stringent conditions with a nucleic acid consisting of a nucleotide sequence complementary to a nucleotide sequence encoding a protein consisting of the amino acid sequence set forth in SEQ ID NO: 2 and that encodes a protein having PAP activity.

The protein consisting of the amino acid sequence set forth in SEQ ID NO: 2 and the hybridization conditions are as described above.

(f) A nucleic acid comprising a nucleotide sequence that is hybridizable under stringent conditions with a nucleic acid consisting of a nucleotide sequence complementary to the nucleotide sequence set forth in SEQ ID NO: 4 and that includes an exon encoding a protein having PAP activity The nucleotide sequences set forth in SEQ ID NO: 4 are the genomic DNA sequences encoding MaPAP2.2.

The nucleotide sequence contained in the nucleic acid of the present invention includes a nucleotide sequence that is hybridizable under stringent conditions with a nucleic acid consisting of a nucleotide sequence complementary to the nucleotide sequence set forth in SEQ ID NO: 4 and that includes an exon encoding a protein having PAP activity.

Such a nucleotide sequence can be prepared by a method known to those skilled in the art from, for example, a genomic library by a known hybridization process, such as colony hybridization, plaque hybridization, or Southern blotting using a probe, which is produced by a method known to those skilled in the art by using an appropriate fragment.

(g) A nucleic acid comprising a nucleotide sequence that has an identity of 70% or more with the nucleotide sequence set forth in SEQ ID NO: 4 and that includes an exon encoding a protein having PAP activity The nucleotide sequence contained in the nucleic acid of the present invention includes a nucleotide sequence that has an identity of at least 70% with the nucleotide sequence set forth in SEQ ID NO: 4 and that encodes a protein having PAP activity. Preferred examples of the nucleotide sequence include those having an identity of at least 75%, more preferably 80% or more (e.g., 85% or more, more preferably 90% or more, and most preferably 95%, 98%, or 99% or more) with the nucleotide sequence set forth in SEQ ID NO: 4 and having an exon encoding a protein having PAP activity. The percent identity between two nucleotide sequences can be determined as described above.

The genomic DNA sequence of SEQ ID NO: 4 is composed of 3 exons and 2 introns. The exon regions correspond to nucleotides 1 to 207, 445 to 582, and 889 to 1632 in SEQ ID NO: 4.

In another embodiment, examples of the nucleotide sequence contained in the nucleic acid of the present invention include nucleotide sequences including intron regions having a nucleotide sequence identity of 100% with the genomic DNA sequence set forth in SEQ ID NO: 4 and exon regions having a nucleotide sequence identity of at least 70% or more, more preferably 75% or more, and more preferably 80% or more (e.g., 85% or more, more preferably 90% or more, and most preferably 95%, 98%, or 99% or more) with the sequence set forth in SEQ ID NO: 4, wherein the exon encodes a protein having PAP activity.

In another embodiment, examples of the nucleotide sequence contained in the nucleic acid of the present invention include nucleotide sequences including exon regions having a nucleotide sequence identity of 100% with the genomic DNA sequence set forth in SEQ ID NO: 4 and intron regions having a nucleotide sequence identity of at least 70% or more, more preferably 75% or more, and more preferably 80% or more (e.g., 85% or more, more preferably 90% or more, and most preferably 95%, 98%, or 99% or more) with the sequence set forth in SEQ ID NO: 4, wherein the intron regions can be eliminated by splicing, and thereby the exon regions are ligated to encode a protein having PAP activity.

In another embodiment, examples of the nucleotide sequence contained in the nucleic acid of the present invention include nucleotide sequences including intron regions having a nucleotide sequence identity of at least 70% or more, more preferably 75% or more, and more preferably 80% or more (e.g., 85% or more, more preferably 90% or more, and most preferably 95%, 98%, or 99% or more) with the genomic DNA sequence set forth in SEQ ID NO: 4 and exon regions having a nucleotide sequence identity of at least 70% or more, more preferably 75% or more, and more preferably 80% or more (e.g., 85% or more, more preferably 90% or more, and most preferably 95% or more, 98% or more, or 99% or more) with the sequence set forth in SEQ ID NO: 5 or SEQ ID NO: 10, wherein the intron regions can be eliminated by splicing, and thereby the exon regions are ligated to encode a protein having PAP activity.

The percent identity between two nucleotide sequences can be determined by the method described above.

Furthermore, the nucleic acids of the present invention include nucleic acids that each consists of a nucleotide sequence having deletion, substitution, or addition of one or more nucleotides in the nucleotide sequence set forth in SEQ ID NO: 1 and encoding a protein having PAP activity. More specifically, a usable nucleic acid include any one of the following nucleotide sequences:

(i) a nucleotide sequence having deletion of one or more (preferably one or several (e.g., 1 to 330, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1;

(ii) a nucleotide sequence having substitution of one or more (preferably one or several (e.g., 1 to 330, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1;

(iii) a nucleotide sequence having addition of one or more (preferably one or several (e.g., 1 to 330, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1; or (iv) a nucleotide sequence with any combination of (i) to (iii) above, wherein the nucleotide sequence encodes a protein having PAP activity.

Another embodiment of the nucleic acid of the present invention also includes a nucleic acid containing a fragment of a nucleotide sequence shown in any one of (a) to (d) below:

(a) the nucleotide sequence set forth in SEQ ID NO: 1;

(b) a nucleotide sequence encoding a protein consisting of the amino acid sequence set forth in SEQ ID NO: 2;

(c) the nucleotide sequence set forth in SEQ ID NO: 4; and (d) the nucleotide sequence set forth in SEQ ID NO: 5.

The nucleotide sequence (a) set forth in SEQ ID NO: 1, the nucleotide sequence (b) encoding a protein consisting of the amino acid sequence set forth in SEQ ID NO: 2, and the nucleotide sequence (d) set forth in SEQ ID NO: 5 are as shown in Table 1. The nucleotide sequence set forth in SEQ ID NO: 4 is also as described above. The fragments of these sequences are ORF, CDS, a biologically active region, a region used as a primer as described later, and a region which may serve as a probe contained in these nucleotide sequences, and may be either naturally occurring or artificially prepared.

The nucleic acid of the present invention includes the following nucleic acids.

(1) A nucleic acid shown in any one of (a) to (g) below:

(a) a nucleic acid comprising a nucleotide sequence encoding a protein consisting of an amino acid sequence with deletion, substitution, or addition of one or more amino acids in the amino acid sequence set forth in SEQ ID NO: 2;

(b) a nucleic acid hybridizable under stringent conditions with a nucleic acid consisting of a nucleotide sequence complementary to the nucleotide sequence set forth in SEQ ID NO: 1;

(c) a nucleic acid comprising a nucleotide sequence encoding a protein consisting of a nucleotide sequence having an identity of 70% or more with the nucleotide sequence set forth in SEQ ID NO: 1; and (d) a nucleic acid comprising a nucleotide sequence encoding a protein consisting of an amino acid sequence having an identity of 70% or more with the amino acid sequence set forth in SEQ ID NO: 2;

(e) a nucleic acid hybridizable under stringent conditions with a nucleic acid consisting of a nucleotide sequence complementary to a nucleotide sequence encoding a protein consisting of the amino acid sequence set forth in SEQ ID NO: 2;

(f) a nucleic acid hybridizable under stringent conditions with a nucleic acid consisting of a nucleotide sequence complementary to the nucleotide sequence set forth in SEQ ID NO: 4; and (g) a nucleic acid comprising a nucleotide sequence encoding a protein consisting of a nucleotide sequence having an identity of 70% or more with the nucleotide sequence set forth in SEQ ID NO: 4.

(2) A nucleic acid described in (1) above, shown in any one of (a) to (g) below:

(a) a nucleic acid comprising a nucleotide sequence encoding a protein consisting of an amino acid sequence with deletion, substitution, or addition of 1 to 130 amino acids in the amino acid sequence set forth in SEQ ID NO: 2;

(b) a nucleic acid hybridizable under conditions of 2×SSC at 50° C. with a nucleic acid consisting of a nucleotide sequence complementary to the nucleotide sequence set forth in SEQ ID NO: 1;

(c) a nucleic acid comprising a nucleotide sequence having an identity of 90% or more with the nucleotide sequence set forth in SEQ ID NO: 1;

(d) a nucleic acid comprising a nucleotide sequence encoding a protein consisting of an amino acid sequence having an identity of 90% or more with the amino acid sequence set forth in SEQ ID NO: 2;

(e) a nucleic acid hybridizable under conditions of 2×SSC at 50° C. with a nucleic acid consisting of a nucleotide sequence complementary to a nucleotide sequence encoding a protein consisting of the amino acid sequence set forth in SEQ ID NO: 2;

(f) a nucleic acid hybridizable under conditions of 2×SSC at 50° C. with a nucleic acid consisting of a nucleotide sequence complementary to the nucleotide sequence set forth in SEQ ID NO: 4; and (g) a nucleic acid comprising a nucleotide sequence having an identity of 90% or more with the nucleotide sequence set forth in SEQ ID NO: 4.

Phosphatidic Acid Phosphatase Protein

The protein of the present invention, which may be either naturally occurring or artificially prepared, includes a protein consisting of the amino acid sequence set forth in SEQ ID NO: 2 and its mutant protein functionally equivalent to the protein. Such a protein consisting of the amino acid sequence set forth in SEQ ID NO: 2 is as described above. The "protein functionally equivalent" refers to proteins having PAP activity described in the section "Nucleic acid encoding phosphatidic acid phosphatase" above.

In the present invention, examples of the proteins functionally equivalent to a protein consisting of the amino acid sequence set forth in SEQ ID NO: 2 include proteins shown in (a) and (b) below:

(a) a protein consisting of an amino acid sequence with deletion, substitution, or addition of one or more amino acids in the amino acid sequence set forth in SEQ ID NO: 2 and having PAP activity; and (b) a protein consisting of an amino acid sequence having an identity of 70% or more with the amino acid sequence set forth in SEQ ID NO: 2 and having PAP activity.

In the above, the amino acid sequence with deletion, substitution, or addition of one or more amino acids in the amino acid sequence set forth in SEQ ID NO: 2 or the amino acid sequence having an identity of 70% or more with the amino acid sequence set forth in SEQ ID NO: 2 is as described in the section "Nucleic acid encoding phosphatidic acid phosphatase of the present invention" above. The "protein having PAP activity" includes mutants of a protein encoded by a nucleic acid comprising the nucleotide sequence set forth in SEQ ID NO: 1; or mutated proteins by many types of modifications such as deletion, substitution, and addition of one or more amino acids in the amino acid sequence set forth in SEQ ID NO: 2, or modified proteins having, for example, modified amino acid side chains or proteins fused with other proteins, wherein these proteins have PAP activity.

The protein of the present invention may be artificially prepared. In such a case, the protein can be produced by chemical synthesis such as a fluorenylmethyloxycarbonyl (Fmoc) chemistry or a t-butyloxycarbonyl (tBoc) chemistry. Furthermore, peptide synthesizers available from Advanced ChemTech, Perkin Elmer, Pharmacia, Protein Technology Instrument, Synthecell-Vega, PerSeptive, Shimadzu Corporation, or other manufacturers may also be used for chemical synthesis.

The protein of the present invention further includes the following proteins:

(1) (a) a protein consisting of an amino acid sequence with deletion, substitution, or addition of one or more amino acids in the amino acid sequence set forth in SEQ ID NO: 2; and (b) a protein consisting of an amino acid sequence having an identity of 80% or more with the amino acid sequence set forth in SEQ ID NO: 2; and (2) a protein according to any one of (a) and (b) below:

(a) a protein consisting of an amino acid sequence with deletion, substitution, or addition of 1 to 110 amino acids in the amino acid sequence set forth in SEQ ID NO: 2; and (b) proteins consisting of an amino acid sequence having an identity of 90% or more with the amino acid sequence set forth in SEQ ID NO: 2.

Cloning of Nucleic Acids

The PAP nucleic acid can be cloned by, for example, screening from a cDNA library using an appropriate probe. The cloning can be performed by PCR amplification using appropriate primers and subsequent ligation to an appropriate vector. The cloned nucleic acid may be further subcloned into another vector.

Commercially available plasmid vectors can be used, such as pBlue-Script SK(+) (Stratagene), pGEM-T (Promega), pAmp (TM: Gibco-BRL), p-Direct (Clontech), or pCR2.1-TOPO (Invitrogen). In PCR amplification, primers may be any regions of the nucleotide sequence set forth in, e.g., SEQ ID NO: 5. For example, primer PAP2.2-1f: 5'-TTCCGTCAGGACACTCCTCCAGT-3' (SEQ ID NO: 6) can be used as an upstream primer, and primer PAP2.2-4r: 5'-GACAATGCCGAGGATCGAGCC-3' (SEQ ID NO: 7) can be used as a downstream primer. For example, PCR is then performed by using these primers and DNA polymerase to act on cDNA prepared from *M. alpina* cells. This procedure can be readily performed by those skilled in the art, for example, in accordance with "Molecular Cloning, A Laboratory Manual 3rd ed." (Cold Spring Harbor Press (2001)). For example, the PCR in the present invention can be performed under the following conditions:

Denaturation temperature: 90° C. to 95° C.,
Annealing temperature: 40° C. to 60° C.,
Elongation temperature: 60° C. to 75° C., and
Number of cycles: 10 or more cycles.

The PCR product can be purified by a known method, for example, a method using a kit such as a GENECLEAN (Funakoshi Co., Ltd.), a QIAquick PCR purification kit (QIAGEN), or an ExoSAP-IT (GE Healthcare Bio-Sciences)); a method using a DEAE-cellulose filter; or a method using a dialysis tube. In the case using an agarose gel, the PCR product is subjected to agarose gel electrophoresis, and nucleotide sequence fragments are cut out from the agarose gel and are purified, for example, with a GENECLEAN (Funakoshi Co., Ltd.) or a QIAquick Gel extraction kit (QIAGEN) or by a freeze-squeeze method.

The nucleotide sequence of the cloned nucleic acid can be determined with a nucleotide sequencer.

Vector Construction for PAP Expression and Preparation of Transformant

The present invention also provides a recombinant vector containing a nucleic acid encoding PAP. The present invention further provides a transformant transformed with such a recombinant vector.

The recombinant vector and transformant can be prepared as follows. A plasmid having a nucleic acid encoding MaPAP2.2 or mutants thereof is digested with a restriction enzyme. Examples of the restriction enzyme include, but not limited to, EcoRI, KpnI, BamHI, and SalI. The end may be blunted with T4 polymerase. A digested DNA fragment is purified by agarose gel electrophoresis. This DNA fragment is incorporated into an expression vector by a known method to prepare a vector for PAP expression. This expression vector is introduced into a host cell to prepare a transformant, which is provided for expression of a desired protein.

In this case, the expression vector and the host may be of any types that allow expression of a desired protein. Examples of the host include fungi, bacteria, plants, animals, and cells thereof. Examples of fungi include filamentous fungi such as lipid-producing M. alpina and yeast strains such as Saccharomyces cerevisiae. Examples of bacteria include Escherichia coli and Bacillus subtilis; and examples of plants include oil-producing plants such as rapeseed, soybean, cotton, safflower, and flax.

Usable lipid-producing microorganisms are, for example, strains described in MYCOTAXON, Vol. XLIV, NO. 2, pp. 257-265 (1992), and specific examples thereof include microorganisms belonging to the genus Mortierella such as microorganisms belonging to subgenus Mortierella, e.g., Mortierella elongata IFO8570, Mortierella exigua IFO8571, Mortierella hygrophila IFO5941, Mortierella alpina IFO8568, ATCC16266, ATCC32221, ATCC42430, CBS 219.35, CBS224.37, CBS250.53, CBS343.66, CBS527.72, CBS528.72, CBS529.72, CBS608.70, and CBS754.68; and microorganisms belonging to subgenus Micromucor, e.g., Mortierella isabellina CBS194.28, IFO6336, IFO7824, IFO7873, IFO7874, IFO8286, IFO8308, IFO7884, Mortierella nana IFO8190, Mortierella ramanniana IFO5426, IFO8186, CBS112.08, CBS212.72, IFO7825, IFO8184, IFO8185, IFO8287, and Mortierella vinacea CBS236.82. In particular, Mortierella alpina is preferred.

In the case using a fungus as a host, the nucleic acid of the present invention is preferably self-replicable in the host or preferably has a structure insertable onto the fungal chromosome. Preferably, the nucleic acid also includes a promoter and a terminator. In the case using M. alpina as a host, for example, pD4, pDuraSC, or pDura5 can be used as the expression vector. Any promoter that allows expression in the host can be used, and examples thereof include promoters derived from M. alpina, such as a histonH4.1 gene promoter, GAPDH (glyceraldehyde-3-phosphate dehydrogenase) gene promoter, and TEF (translation elongation factor) gene promoter.

Examples of the method introducing a recombinant vector into filamentous fungi such as M. alpina include electroporation, a spheroplast method, a particle delivery method, and direct microinjection of DNA into nuclei. In the case using an auxotrophic host strain, the transformed strain can be obtained by selecting a strain that grows on a non-nutritive selective medium. Alternatively, in transformation using a drug resistant-marker gene, a colony of drug-resistant cells can be obtained by culturing the host cells in a selective medium containing the drug.

In the case using yeast as a host, for example, pYE22m can be used as the expression vector. Alternatively, commercially available yeast expression vectors such as pYES (Invitrogen) and pESC (STRATAGENE) may be used. Examples of the host suitable for the present invention include, but not limited to, Saccharomyces cerevisiae strain EH13-15 (trp1, MATα). Examples of the promoter that can be used include promoters derived from yeast, such as a GAPDH promoter, a gal1 promoter, and a gal10 promoter.

Examples of the method for introducing a recombinant vector into yeast include a lithium acetate method, electroporation, a spheroplast method, dextran-mediated transfection, calcium phosphate precipitation, polybrene-mediated transfection, protoplast fusion, encapsulation of polynucleotide(s) in liposomes, and direct microinjection of DNA into nuclei.

In the case using a bacterium such as E. coli as a host, for example, pGEX and pUC18 available from Pharmacia can be used as the expression vector. Examples of the promoter include those derived from, for example, E. coli or phage, such as a trp promoter, a lac promoter, a PL promoter, and a PR promoter. Examples of the method of introducing a recombinant vector into bacteria include electroporation and a calcium chloride method.

Method of Preparing Fatty Acid Composition

The present invention provides a method of preparing a fatty acid composition from the transformant described above, i.e., a method of preparing a fatty acid composition from a cultured product obtained by culturing the transformant. The fatty acid composition includes a combination of one or more fatty acids therein. The fatty acids may be present in the form of free fatty acids or lipids thereof such as triglyceride or phospholipid. Specifically, the fatty acid composition of the present invention can be prepared by the following methods. The present methods are not, however, limited to those below, but, the fatty acid composition can also be prepared by any other known method.

The medium used for culturing an organism expressing PAP may be any culture solution (medium) that has an appropriate pH and osmotic pressure and contains biomaterials such as nutrients, trace elements, sera, and antibiotics necessary for growth of each host. For example, in the case of expression of PAP by transforming yeast, unlimited examples of the medium for use include SC-Trp media, YPD media, and YPD5 media. A typical example of the composition of a specific medium, i.e., SC-Trp medium, is as follows: one liter of the medium includes 6.7 g of yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil).

Any culture condition suitable for host growth and adequate for stably retaining the produced enzyme may be employed. Specifically, individual conditions, such as anaerobic degree, culture period, temperature, humidity, and static culture or shake culture, can be adjusted. Culture may be accomplished under the same condition (one-step culture) or by so-called two-step or three-step culture including two or more different culture conditions. For large-scale culture, two- or more-step culture is preferred because of its high culture efficiency.

In two-step culture using yeast as a host, the fatty acid composition of the present invention can be prepared as follows: In pre-culture, a colony of a transformant is inoculated in, for example, a SC-Trp medium and shake-cultured at 30° C. for two days. Subsequently, in main culture, 500 μL of pre-culture solution is added to 10 mL of YPD5 (2% yeast extract, 1% polypeptone, and 5% glucose) medium, followed by shake culture at 30° C. for two days.

Fatty Acid Composition

The present invention also provides a fatty acid composition comprising aggregates of one or more fatty acids in cells expressing MaPAP2.2 and mutants thereof, preferably, a fatty acid composition obtained by culturing a transformant expressing Ma PAP2.2 and mutants thereof. The fatty acids may be present in the form of fatty acids or lipids thereof such as triglyceride or phospholipid.

The fatty acids contained in the fatty acid composition of the present invention are 1 monocarboxylic acids of inear or branched long-chain carbohydrates, and examples thereof include, but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), margaric acid (heptadecanoic acid) (17:0), stearic acid (octadecanoic acid) (18:0), oleic acid (cis-9-octadecenoic acid) (18:1(9)), vaccenic acid (11-octadecenoic acid) (18:1(11)), linolic acid (cis,cis-9,12 octadecadienoic acid) (18:2(9,12)), α-linolenic acid (9,12,15-octadecatrienoic acid) (18:3(9,12,15)), γ-linolenic acid (6,9,12-octadecatrienoic acid) (18:3(6,9,12)), stearidonic acid (6,9,12,15-octadecatetraenoic acid) (18:4(6,9,12,15)), arachidic acid (icosanoic acid) (20:0), (8,11-icosadienoic acid) (20:2(8,11)), mead acid (5,8,11-icosatrienoic acid) (20:3(5,8,11)), dihomo-γ-linolenic acid (8,11,14-icosatrienoic acid) (20:3(8,11,14)), arachidonic acid (5,8,11,14-icosatetraenoic acid) (20:4(5,8,11,14)), eicosatetraenoic acid (8,11,14,17-icosatetraenoic acid) (20:4(8,11,14,17)), eicosapentaenoic acid (5,8,11,14,17-icosapentaenoic acid) (20:5(5,8,11,14,17)), behenic acid (docosanoic acid) (22:0), (7,10,13,16-docosatetraenoic acid) (22:4(7,10,13,16)), (7,10,13,16,19-docosapentaenoic acid) (22:5(7,10,13,16,19)), (4,7,10,13,16-docosapentaenoic acid) (22:5(4,7,10,13,16)), (4,7,10,13,16,19-docosahexaenoic acid) (22:6(4,7,10,13,16,19)), lignoceric acid (tetracosanoic acid) (24:0), nervonic acid (cis-15-tetracosenoic acid) (24:1), and cerotic acid (hexacosanoic acid) (26:0). Note that the substance names are common names defined by the IUPAC Biochemical Nomenclature, and their systematic names are given in parentheses along with numerics denoting the number of carbons and the positions of double bonds.

In the fatty acid composition of the present invention, these fatty acids may be used alone or in combination of two or more different fatty acids.

Food or Other Products Comprising Fatty Acid Composition

The present invention also provides a food product comprising the fatty acid composition described above. The fatty acid composition of the present invention can be used for production of food products containing fats and oils and production of industrial raw materials (for example, raw materials for cosmetics, pharmaceuticals (e.g., external applications for the skin), and soaps), in usual methods. Cosmetics (cosmetic compositions) or pharmaceuticals (pharmaceutical compositions) may be formulated into any dosage form including, but not limited to, solution, paste, gel, solid, and powder. Examples of the forms of food products include pharmaceutical formulations such as capsule; natural liquid diet, semi-digested nutritious diet, and elemental nutritious diet where the fatty acid composition of the present invention is blended with proteins, sugars, fats, trace elements, vitamins, emulsifiers, and flavorings; and processed forms such as drinkable preparations and enteral nutrients.

Moreover, examples of the food product of the present invention include, but not limited to, nutritional supplements, health food, functional food, infant food, modified milk for infants, modified milk for premature infants, and geriatric food. The term "food" is used herein as a collective term for edible materials in the form of solid, fluid, liquid, or a mixture thereof.

The term "nutritional supplements" refers to food products enriched with specific nutritional ingredients. The term "health food" refers to food products that are healthful or good for health and includes nutritional supplements, natural food, and diet food. The term "functional food" refers to food products for supplying nutritional ingredients that assist body control functions and is synonymous with food for specified health use. The term "infant food" refers to food products given to children up to about 6 years old of age. The term "geriatric food" refers to food products treated to facilitate digestion and absorption thereof, compared to untreated food. The term "modified milk for infants" refers to modified milk given to children up to about one year of age. The term "modified milk for premature infants" refers to modified milk given to premature infants until about 6 months after birth.

Examples of these food products include natural food (treated with fat and oil) such as meat, fish, and nuts; food supplemented with fat and oil during preparation, such as Chinese foods, Chinese noodles, and soups; food products prepared using fat and oil as a heating medium, such as tempura (deep-fried fish and vegetables), deep-fried food, fried tofu, Chinese fried rice, doughnuts, and Japanese fried dough cookies (karinto)); fat- and oil-based food or processed food supplemented with fat and oil during processing, such as butter, margarine, mayonnaise, dressing, chocolate, instant noodles, caramel, biscuits, cookies, cake, and ice cream; and food sprayed or coated with fat and oil upon finishing, such as rice crackers, hard biscuits, and sweet bean paste bread (anpan). The food products of the present invention, however, are not limited to food containing fat and oil, and other examples thereof include agricultural food products such as bakery products, noodles, cooked rice, sweets (e.g., candies, chewing gums, gummies, tablets, Japanese sweets), tofu, and processed products thereof; fermented food products such as refined sake, medicinal liquor, seasoning liquor (mirin), vinegar, soy sauce, and miso; livestock food products such as yogurt, ham, bacon, and sausage; seafood products such as fish paste (kamaboko), deep-fried fish paste (ageten), and fish cake (hanpen); and fruit drinks, soft drinks, sports drinks, alcoholic beverages, and tea.

Method for Evaluating or Selecting Strains Using PAP-Encoding Nucleic Acid or PAP Protein The present invention also provides a method for evaluating or selecting a lipid-producing fungus using the PAP-encoding nucleic acid or PAP protein of the present invention. Details are given below.

(1) Method for Evaluation

One embodiment of the present invention is a method of evaluating a lipid-producing fungus using the PAP-encoding nucleic acid or the PAP protein of the present invention. In the method for evaluation of the present invention, for example, a lipid-producing fungus strain as a test strain is evaluated for PAP activity using primers or probes designed based on the nucleotide sequence of the PAP-encoding nucleic acid of the present invention. Such evaluation can be performed by known procedures, for example, described in International Publication No. WO01/040514 and JP-A-8-205900. The method for evaluation will be briefly described below.

The first step is preparation of a genome of a test strain. The genome can be prepared by any known method such as a Hereford method or a potassium acetate method (see, e.g., Methods in Yeast Genetics, Cold Spring Harbor Laboratory Press, p. 130 (1990)).

Primers or probes are designed based on the nucleotide sequence of the PAP-encoding nucleic acid of the present invention, preferably the sequence set forth in SEQ ID NO: 1. These primers or probes may be any regions of the nucleotide sequence of the PAP-encoding nucleic acid of the present invention and may be designed by a known procedure. The number of nucleotides in a polynucleotide used for a primer is generally 10 or more, and preferably 15 to 25. The number of nucleotides appropriate for a region between the primers is generally 300 to 2000.

The primers or probes prepared above are used to examine whether the genome of a test strain contains a sequence specific to the nucleotide sequence of the PAP-encoding nucleic acid of the present invention. The sequence specific to the nucleotide sequence of the present invention can be detected by any known procedure. For example, a polynucleotide comprising a part of the nucleotide sequence of the PAP-encoding nucleic acid of the present invention or a polynucleotide comprising a nucleotide sequence complementary to the nucleotide sequence is used as one primer while a polynucleotide containing a part of a sequence located upstream or downstream of this sequence or a polynucleotide comprising a nucleotide sequence complementary to the nucleotide sequence is used as the other primer, and a nucleic acid from the test strain is amplified by PCR or any other technique. This procedure can confirm the presence of an amplification product and determine the molecular weight of the amplification product.

PCR conditions suitable for the method of the present invention may be employed without any restriction, and are, for example, as follows:

Denaturation temperature: 90° C. to 95° C.
Annealing temperature: 40° C. to 60° C.
Elongation temperature: 60° C. to 75° C.
Number of cycles: 10 or more cycles.

The reaction products can be separated by electrophoresis on an agarose gel or any other process to determine the molecular weight of the amplification product. Thus, the PAP activity of the test strain can be predicted or evaluated by confirming whether the molecular weight of the amplification product is enough to cover a nucleic acid molecule corresponding to a region specific to the nucleotide sequence of the present invention. Furthermore, the analysis of the nucleotide sequence of the amplification product using the method described above enables the PAP activity to be more accurately predicted or evaluated. The method of evaluating the PAP activity is as described above.

Alternatively, in the evaluation according to the present invention, the PAP activity of a test strain may be evaluated by culturing the test strain and measuring the expression level of the PAP encoded by the nucleotide sequence of the present invention, e.g., the sequence set forth in SEQ ID NO: 1. The expression level of the PAP can be measured by culturing the test strain under appropriate conditions and quantitatively determining the mRNA or protein for the PAP. The mRNA and protein can be quantified by any known procedure. For example, mRNA can be quantified by Northern hybridization or quantitative RT-PCR, and protein can be quantitatively determined by Western blotting (Current Protocols in Molecular Biology, John Wiley & Sons, 1994-2003).

(2) Method for Selection

Another embodiment of the present invention is a method of selecting a lipid-producing fungus using a PAP-encoding nucleic acid or PAP protein of the present invention. In the selection according to the present invention, a strain having a desired activity can be selected by culturing a test strain, measuring the expression level of the PAP encoded by the nucleotide sequence of the present invention, e.g., sequence set forth in SEQ ID NO: 1, and selecting a strain of a desired expression level. Alternatively, a desired strain can be selected by establishing a standard strain, culturing the standard strain and a test strain separately, measuring the expression level of each strain, and comparing the expression level of the standard strain with that of the test strain. Specifically, for example, a standard strain and test strains are cultured under appropriate conditions, and the expression level of each strain is measured. A strain exhibiting a desired activity can be selected by selecting a test strain showing higher or lower expression than the standard strain does. The desired activity can be determined by, for example, measuring the expression level of PAP and the compositional ratio of fatty acid composition produced by the PAP, as described above.

In the selection according to the present invention, a test strain having a desired activity can be selected by culturing test strains and selecting a strain having high or low activity of the present invention. The desired activity can be determined by, for example, measuring the expression level of PAP and the compositional ratio of fatty acid composition produced by the PAP, as described above.

Examples of the test strain and the standard strain include, but not limited to, strains transformed with the vector of the present invention, strains modified to suppress expression of the nucleic acid of the present invention, mutagenized strains, and naturally mutated strains. The PAP activity can be measured by, for example, the method described herein in the section "Nucleic acid encoding phosphatidic acid phosphatase of the present invention". Examples of the mutagenesis include, but not limited to, physical approaches such as UV or radioactive irradiation, and chemical approaches such as chemical treatments with, for example, EMS (ethylmethane sulfonate) or N-methyl-N-nitrosoguanidine (see, e.g., Yasuji Oshima ed., Biochemistry Experiments vol. 39, Experimental Protocols for Yeast Molecular Genetics, pp. 67-75, Japan Scientific Societies Press).

Examples of the strains used as the standard strain and the test strain of the present invention include, but not limited to, the lipid-producing fungus and yeast described above. Specifically, the standard strain and the test strain may be any combination of strains belonging to different genera or species, and one or more test strains may be simultaneously used.

The following examples further illustrate the present invention, but are not intended to limit the scope of the present invention.

EXAMPLES

Example 1

Genomic Analysis of *Mortierella alpina*

*M. alpina* strain 1S-4 was inoculated into 100 mL of a GY2:1 medium (2% glucose, 1% yeast extract, pH 6.0) and was shake-cultured at 28° C. for 2 days. The cells were collected by filtration to prepare genomic DNA using DNeasy (QIAGEN).

The nucleotide sequence of the genomic DNA was determined with a Roche 454 GS FLX Standard. This involved two runs of nucleotide sequencing of a fragment library and three runs of mate pair library sequencing. The resulting nucleotide sequences were assembled into 300 supercontigs.

Example 2

Synthesis of cDNA and Preparation of a cDNA Library

M. alpina strain 1S-4 was inoculated into 100 mL of a medium (1.8% glucose, 1% yeast extract, pH 6.0) and was pre-cultured at 28° C. for 3 days. A 10 L culture vessel (Able Co., Tokyo) was charged with 5 L of a medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) and inoculated with the entire pre-cultured product, followed by aerobic spinner culture under conditions of 300 rpm, 1 vvm and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl procedure. Using an Oligotex-dT30<Super>mRNA Purification Kit (Takara Bio Inc.), poly (A)+ RNA was purified from the total RNA. A cDNA library for each stage was prepared with a ZAP-cDNA GigapackIII Gold Cloning Kit (STRATAGENE).

Example 3

Search for DPP1 Homologs Derived from Yeast

Genome database was searched for homologs of ScDPP1 (YDR284C: accession number AAS56070) and ScLPP1 (YDR503C: accession number AAT93210). As a result, two supercontigs were identified. One is a supercontig including the genome sequence of MaPAP1, and the other is a superconting including SEQ ID NO: 4. The gene of SEQ NO ID: 4 was named MaPAP2.2.

Example 4

Cloning and Sequencing Analysis of MaPAP2.2

(1) Cloning
The following primers were prepared for cloning of cDNA of MaPAP2.2.

```
                                        (SEQ ID NO: 6)
Primer PAP2.2-1f: TTCCGTCAGGACACTCCTCCAGT (SEQ ID NO: 7)
Primer PAP2.2-4r: GACAATGCCGAGGATCGAGCC
```

The library prepared above was used as a template to perform PCR with ExTaq (Takara Bio Inc.) in at 94° C. for 2 minutes, and 30 cycles of 94° C. for 1 minute, 55° C. for 1 minute, and 72° C. for 1 minute, using the combination of primers, PAP2.2-1F and PAP2.2-4R. The approximately 0.4 kbp DNA fragment obtained was cloned with a TOPO-TA Cloning Kit (Invitrogen) to determine the nucleotide sequence for each insert. The plasmid containing the nucleotides 534 to 904 in the sequence set forth in SEQ ID NO: 3 was named pCR-MaPAP2.2-P.

Then, the plasmid pCR-MaPAP2.2-P was used as a template to perform PCR with the above primers for preparation of a probe. ExTaq (Takara Bio Inc.) was used for the reaction, but a PCR labeling mix (Roche Diagnostics) was used instead of the dNTP mix included in the kit to prepare a probe (MaPAP2.2 probe) labeled with digoxigenin (DIG) from the DNA to be amplified. This probe was used to screen the cDNA library.

Hybridization conditions are as follows.

Buffer: 5×SSC, 1% SDS, 50 mM Tris-HCl (pH 7.5), 50% formamide;

Temperature: 42° C. (overnight);

Washing conditions: 3 times in a solution of 0.2×SSC, 0.1% SDS (65° C.) for 20 minutes.

Detection was carried out with a DIG nucleic acid detection kit (Roche Diagnostics). Plasmids were excised by in vivo excision from phage clones obtained by screening to yield each plasmid DNA. The plasmid having the longest insert contains the nucleotide sequence set forth in SEQ ID NO: 5, and was named plasmid pB-MaPAP2.2.

The nucleotides 75 to 1166 in SEQ ID NO: 5 (the same as in SEQ ID NO: 3) were identified as the CDS of MaPAP2.2 based on the presence of start and stop condons and other comparisons with PAP2 homologs.

(2) Sequence Analysis

Homology searches of the nucleotide sequence of the MaPAP2.2 gene and the deduced amino acid sequence encoded thereby were performed against known nucleic acid and amino acid sequences with BLAST and clustalW analysis. Among sequences identified in the homology search against amino acid sequences registered in GENBANK with BLASTX, a sequence having the lowest E-Value was a putative protein derived from Laccaria bicolor (accession No: XP_001878243), which had an amino acid sequence identity of 36.7%. FIG. 2 shows an alignment of amino acid sequences of MaPAP2.2 with a putative protein derived from Laccaria bicolor and ScDPP1 (YDR284C: accession number AAS56070) derived from yeast.

The amino acid sequence identity between MaPAP1 known as a $Mg^{2+}$-independent PAP (PAP2) derived from Mortierella alpina (WO 2009/008466) and MaPAP2.2 was about 20.5%. An alignment of amino acid sequences of MaPAP2.2 and MaPAP1 are shown in FIG. 3. PAP2 family enzymes contain three conserved regions, and amino acids essential for their activity are also known. As shown in FIG. 3, MaPAP2.2 also contains these conserved regions (double-underlined in FIG. 3) and the residues essential for the activity, i.e., arginine in domain 1 and histidines in domains 2 and 3 (residues indicated with * in FIG. 3).

Example 5

Functional Analysis of MaPAP2.2

(1) Construction of Yeast Expression Vector

To express MaPAP2.2 in yeast cells, yeast expression vectors were constructed as follows. Primers, Eco-PAP2-2-F and Kpn-PAP2-2-R, were prepared, followed by PCR ExTaq (Takara Bio Inc.) using the pB-MaPAP2.2 as a template.

Primer Eco-PAP2-2-F: (SEQ ID NO: 8)

GAATTC<u>ATG</u>TTCTCGTCCATGCGCTTCAAG

Primer Kpn-PAP2-2-R: (SEQ ID NO: 9)

TGGTACC<u>TCA</u>TGGTCCCAAGTATACATCGTTCC

The resulting DNA fragment of 1.1 kbp was TA-cloned with a TOPO-TA cloning Kit (Invitrogen) for confirmation of its nucleotide sequence. A plasmid carrying the correct CDS nucleotide sequence (SEQ ID NO: 3) of MaPAP2.2 was named pCR-MaPAP2.2. A fragment of about 1.1 kbp DNA, generated by digestion of the plasmid pCR-MaPAP2.2 with restriction enzymes EcoRI and KpnI, and a fragment of about 8.3 kbp DNA, generated by yeast expression vector pYE22m (Biosci. Biotech. Biochem., 59, 1221-1228, 1995) with restriction enzymes EcoRI and KpnI, were ligated with Ligation High (TOYOBO) to construct a plasmid pYE-MaPAP2.2.

(2) Acquisition of Transformed Yeast

Each of the plasmid pYE22m, pYE-MaPAP2.2 and pYE-MaPAP1 (WO2009/008466) was used to transform yeast S. cerevisiae strain EH13-15 (trp1, MATα) (Appl. Microbiol. Biotechnol., 30, 515-520, 1989) by the lithium acetate method. The transformed strains were screened for the ability to grow on a SC-Trp agar medium (2% agar) containing 6.7 g Yeast nitrogen base w/o amino acids (DIFCO), 20 g glucose, and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine, and 0.6 g uracil) per liter of medium.

(3) Yeast Culture

The transformed strains obtained with each vector were cultured under the following conditions. In the pre-culture step, yeast is inoculated in 10 mL SD-Trp and cultured with shaking at 30° C. for 1 day. In the main culture step, the pre-cultured solution (1 mL) was added to 100 mL SD-Trp and the mixture was cultured with shaking at 30° C. for 1 day.

(4) Preparation of Crude Enzyme Solution

The cells were collected by centrifugation, washed with water, and temporarily stored at −80° C. Buffer A (5 mL: 50 mM Tris-HCl (pH 7.5), 0.3 M sucrose, 10 mM DTT, 1 M PMSF) was added to the cells to suspend the cells therein. Then, the cells were disrupted with a French press (16 kPa, three times). The disrupted cell suspension was centrifuged at 1,500×g at 4° C. for 10 minutes, and the resulting supernatant was used as a crude enzyme solution.

(5) Determination of PAP Activity

Procedure

The PAP activity was measured as follows. A reaction solution was prepared in a total volume 500 μL containing 50 mM Tris-HCl (pH7.5), 50 μg of linoleic acid (18:2)—PA, oleic acid (18:1)—PA, or margaric acid (17:0)—PA (phosphatidic acid as a substrate), 0.5 mM MgCl$_2$ or 0.5 mM EDTA, 10 mM DTT, and 100 μL of the crude enzyme solution, and the mixture was allowed to react at 28° C. for 30 minutes. A mixture of chloroform and methanol (1:2) was added to the reaction mixture to quench the reaction. A reaction solution containing the supernatant of the cell homogenate of yeast (control strain) transformed by plasmid pYE22m containing no MaPAP2.2 gene, instead of the crude enzyme solution, was used as a control. Lipids were extracted by the method of Bligh & Dyer, treated by a centrifugal concentrator to dryness, dissolved in chloroform, and then fractionated by TLC (Silica gel 60 plate, hexane:diethylether:acetic acid=70:30:1). The plate was sprayed with primulin solution to visualize the lipids under UV irradiation, and then fractions of phospholipids and diglyceride (DG) were scraped. All the fatty acids contained in the fractions were converted into methyl esters to be analyzed by gas chromatography.

The PAP activity can be determined by measuring the conversion of the diglyceride (DG) from the phosphatidic acid (PA) added as a substrate.

Results

The results were shown in FIGS. 4 to 7.

As shown in FIG. 4, the amounts of 18:2-DG increased in the reaction solutions with the addition of the crude enzyme solution of MaPAP2.2, compared with the controls. This demonstrates that the conversion of 18:2-PA to 18:2-DG increased due to the presence of MaPAP2.2, meaning that MaPAP2.2 has the PAP activity. Furthermore, as can be seen from the results in FIG. 4, the extent of conversion of 18:2-PA to 18:2-DG was comparable between the control and the highly expressed strain of MaPAP2.2 (designated as MaPAP2.2 in FIG. 4), regardless of the presence or absence of Mg$^{2+}$, clearly indicating that MaPAP2.2 has the same PAP activity regardless of the presence or absence of Mg$^{2+}$, that is, the PAP activity of MaPAP2.2 is independent of Mg$^{2+}$.

FIG. 5 shows graphs illustrating the results of investigation on the amount of 18:2-DG in a Mg$^{2+}$-free reaction solution including the crude enzyme solution of MaPAP2.2 or MaPAP1. MaPAP2.2 increased the conversion of 18:2-PA to 18:2-DG significantly, while MaPAP1 yielded only the same amount of 18:2-DG as controls. These results indicate that MaPAP2.2 and MaPAP1 are different in substrate specificity.

FIG. 6 shows the results of investigation on the amount of 18:1-DG after the reaction with or without the addition of 18:1-PA as a substrate in the reaction solutions containing the crude enzyme solution of MaPAP2.2 and the controls. The amounts of 18:1-PA (background) were measured under conditions without the addition of 18:1-PA because 18:1-PA is phosphatidic acid originally present in yeast, and no difference was found between the expressed strains of MaPAP2.2 and control strains (FIG. 6A). Then, the amounts of 18:1-DG after the reaction with the addition of 18:1-PA were measured. The results demonstrated that a more amount of 18:1-PA was produced in the case using the crude enzyme solution of the control than in the case using the crude enzyme solution of MaPAP2.2 (FIG. 6B). This result shows that MaPAP2.2 has the PAP activity even when 18:1-PA is used as a substrate.

FIG. 7 shows the results of comparison of the amounts of 17:0-DG after the reaction between addition of 17:0-PA as a substrate to the reaction solution containing the crude enzyme solution of MaPAP2.2 and addition thereof to the control. The result in FIG. 7 shows that MaPAP2.2 has PAP activity even in the case using 17:0-PA as a substrate.

Comparison of the results shown in FIGS. 5 to 7 shows the activity of converting 18:2-PA to 18:2-DG was comparable with that of converting 18:1-PA to 18:1-DG, while the activity of converting 17:0-PA to 17:0-DG was about one fifth of the activity of converting 18:2-PA to 18:2-DG or 18:1-PA to 18:1-DG. This indicates that the phosphatidic acid phosphatase activity of MaPAP2.2 has a higher substrate specificity for a $C_{18}$ acyl group-containing phosphatidic acid than for a $C_{17}$ acyl group-containing one.

SEQUENCE LISTING FREE TEXT

SEQ ID NO: 6: primer PAP2.2-1f
SEQ ID NO: 7: primer PAP2.2-4r
SEQ ID NO: 8: primer Eco-PAP2-2-F
SEQ ID NO: 9: primer Kpn-PAP2-2-R

The invention claimed is:

1. A nucleic acid comprising:
(a) a nucleotide sequence that has an identity of 95% or more with the nucleotide sequence set forth in SEQ ID NO: 1 and that encodes a protein having the ability to catalyze the reaction of generating diacylglycerol by dephosphorylation of phosphatidic acid;
(b) an intron-free nucleotide sequence encoding a protein that consists of an amino acid sequence having an identity of 95% or more with the amino acid sequence set forth in SEQ ID NO: 2 and that has the ability to catalyze the reaction of generating diacylglycerol by dephosphorylation of phosphatidic acid;
(c) a nucleotide sequence that has an identity of 95% or more with the nucleotide sequence set forth in SEQ ID NO: 3 and that encodes a protein having the ability to catalyze the reaction of generating diacylglycerol by dephosphorylation of phosphatidic acid; or (d) a nucleotide sequence that has an identity of 95% or more with the nucleotide sequence set forth in SEQ ID NO: 5 and that encodes a protein having the ability to catalyze the reaction of generating diacylglycerol by dephosphorylation of phosphatidic acid.

2. A cDNA comprising a nucleic acid according to any one of (a)-(e) below:
(a) a nucleotide sequence encoding a protein that consists of an amino acid sequence with deletion, substitution, or addition of 1 to 15 amino acids in the amino acid sequence set forth in SEQ ID NO: 2 and that has the ability to catalyze the reaction of generating diacylglycerol by dephosphorylation of phosphatidic acid;
(b) a nucleotide sequence that has an identity of 95% or more with the nucleotide sequence set forth in SEQ ID NO: 1 and that encodes a protein having the ability to catalyze the reaction of generating diacylglycerol by dephosphorylation of phosphatidic acid;
(c) a nucleotide sequence encoding a protein that consists of an amino acid sequence having an identity of 95% or more with the amino acid sequence set forth in SEQ ID NO: 2 and that has the ability to catalyze the reaction of generating diacylglycerol by dephosphorylation of phosphatidic acid;
(d) a nucleotide sequence that has an identity of 95% or more with the nucleotide sequence set forth in SEQ ID NO: 3 and that encodes a protein having the ability to catalyze the reaction of generating diacylglycerol by dephosphorylation of phosphatidic acid; or (e) a nucleotide sequence that has an identity of 95% or more with the nucleotide sequence set forth in SEQ ID NO: 5 and that encodes a protein having the ability to catalyze the reaction of generating diacylglycerol by dephosphorylation of phosphatidic acid.

3. The nucleic acid according to claim 1, wherein the nucleic acid comprises:
(a) the nucleotide sequence set forth in SEQ ID NO: 1;
(b) the nucleotide sequence set forth in SEQ ID NO: 3; or
(c) the nucleotide sequence set forth in SEQ ID NO: 5.

4. The nucleic acid according to claim 1, wherein the ability to catalyze the reaction of generating diacylglycerol by dephosphorylation of phosphatidic acid has a higher substrate specificity for a $C_{18}$ acyl group-containing phosphatidic acid than for a $C_{17}$ acyl group-containing one.

5. The cDNA according to claim 2, wherein the ability to catalyze the reaction of generating diacylglycerol by dephosphorylation of phosphatidic acid has a higher substrate specificity for a $C_{18}$ acyl group-containing phosphatidic acid than for a $C_{17}$ acyl group-containing one.

6. A recombinant vector comprising the nucleic acid according to claim 1.

7. A transformant transformed with the recombinant vector according to claim 6, wherein the transformant is a host cell selected from a bacterial cell, a fungal cell, an isolated plant cell, or an isolated animal cell.

8. A recombinant vector comprising the cDNA according to claim 2.

9. A transformant transformed with the recombinant vector according to claim 8, wherein the transformant is a host cell selected from a bacterial cell, a fungal cell, an isolated plant cell, or an isolated animal cell.

* * * * *

```
                        SEQUENCE LISTING

<160> NUMBER OF SEQ ID NOS: 12

<210> SEQ ID NO 1
<211> LENGTH: 1089
<212> TYPE: DNA
<213> ORGANISM: Mortierella alpina
<220> FEATURE:
<221> NAME/KEY: CDS
<222> LOCATION: (1)..(1089)

<400> SEQUENCE: 1 atg ttc tcg tcc atg cgc ttc aag gcc cgg aca agg tcc ttg ttt ctc      48
Met Phe Ser Ser Met Arg Phe Lys Ala Arg Thr Arg Ser Leu Phe Leu
1               5                   10                  15 tcc tat gtc aag gac tgg ggt ctg gtg att gtg atc ctg gcc gtc ttc      96
Ser Tyr Val Lys Asp Trp Gly Leu Val Ile Val Ile Leu Ala Val Phe
            20                  25                  30 tct tac gtc gac aca ctc gag cca ttc cat cgc cag ttc tct gtc caa     144
Ser Tyr Val Asp Thr Leu Glu Pro Phe His Arg Gln Phe Ser Val Gln
        35                  40                  45 gac atg tcc att cag cat ccc tat gca aag aag gag acg gtt cct gta     192
Asp Met Ser Ile Gln His Pro Tyr Ala Lys Lys Glu Thr Val Pro Val
    50                  55                  60 tgg atg gcg ctg gta ctt gct ttc att ctc ccc gct gtt gtt att ggg     240
Trp Met Ala Leu Val Leu Ala Phe Ile Leu Pro Ala Val Val Ile Gly
65                  70                  75                  80 ctt att gcc ctc ctc aag aga aga tcc tac acg gat ttt cac aac gga     288
Leu Ile Ala Leu Leu Lys Arg Arg Ser Tyr Thr Asp Phe His Asn Gly
                85                  90                  95 gta ctt ggc ctc ttt ctt act cag gcc ctc gtt ctt att gta act gac     336
Val Leu Gly Leu Phe Leu Thr Gln Ala Leu Val Leu Ile Val Thr Asp
            100                 105                 110 agc atc aag att gct gtt ggc aga cct cgt cct gac ttt ctg gat cgc     384
Ser Ile Lys Ile Ala Val Gly Arg Pro Arg Pro Asp Phe Leu Asp Arg
        115                 120                 125 tgc ctt gac ttg tac gat aac caa gca gcg ggc aca ccc cta gga cct     432
Cys Leu Asp Leu Tyr Asp Asn Gln Ala Ala Gly Thr Pro Leu Gly Pro
    130                 135                 140 ctc tcg gat cca atc aac atg cta tca aac tcg acc att tgc acc agg     480
Leu Ser Asp Pro Ile Asn Met Leu Ser Asn Ser Thr Ile Cys Thr Arg
145                 150                 155                 160 aca cac ttg ctg aga gat gga ttc aaa tcg ttc ccc tcg gga cat tcc     528
Thr His Leu Leu Arg Asp Gly Phe Lys Ser Phe Pro Ser Gly His Ser
                165                 170                 175 tcc ttt tca ttc gga gga ctg ggc tac ttg tcc atg ttt ctt gca ggc     576
Ser Phe Ser Phe Gly Gly Leu Gly Tyr Leu Ser Met Phe Leu Ala Gly
            180                 185                 190 aag ctg cat ctg ttt gac gag cgt gga cat atc tat aaa tcg gtc gta     624
Lys Leu His Leu Phe Asp Glu Arg Gly His Ile Tyr Lys Ser Val Val
        195                 200                 205 gtt ctg gcg cct ttg atc gtc gct gct ttg atc gct acc tcg cgc gtg     672
Val Leu Ala Pro Leu Ile Val Ala Ala Leu Ile Ala Thr Ser Arg Val
    210                 215                 220 gac gac tac agg cac cat tgg cag gat gtc acc gtc gga gcc ttc att     720
Asp Asp Tyr Arg His His Trp Gln Asp Val Thr Val Gly Ala Phe Ile
```

```
                      225                 230                 235                 240
gga gcc aca ttt gcc atc ttt tcc tac cgt cag tac tac cct tcc ttg         768
Gly Ala Thr Phe Ala Ile Phe Ser Tyr Arg Gln Tyr Tyr Pro Ser Leu
                245                 250                 255 gcg agt tct aaa tcc gac tgc ccc ttc gcg cct cgc att ggc aag gac         816
Ala Ser Ser Lys Ser Asp Cys Pro Phe Ala Pro Arg Ile Gly Lys Asp
                260                 265                 270 gag cat ttg ccg gca gca ctg ttg cct cat cac cat atc cac cga cac         864
Glu His Leu Pro Ala Ala Leu Leu Pro His His His Ile His Arg His
                275                 280                 285 gac aac gag gtg gtg gag gca gag gac gaa gtg cat cgg gaa tcg ttt         912
Asp Asn Glu Val Val Glu Ala Glu Asp Glu Val His Arg Glu Ser Phe
            290                 295                 300 ctg agt aat gtc ggg ggc gcg ggt tcg aat cgg tct cac gag tct ttg         960
Leu Ser Asn Val Gly Gly Ala Gly Ser Asn Arg Ser His Glu Ser Leu
305                 310                 315                 320 acg gga gga acg agt ctg cag gat ctg agt aac aat cat cat ggg gcc        1008
Thr Gly Gly Thr Ser Leu Gln Asp Leu Ser Asn Asn His His Gly Ala
                325                 330                 335 aag ctc aac agc acg gcg ggc tat ggc ttt gat cag cag cgt aat gga        1056
Lys Leu Asn Ser Thr Ala Gly Tyr Gly Phe Asp Gln Gln Arg Asn Gly
                340                 345                 350 ggt ggt caa cgg aac gat gta tac ttg gga cca                            1089
Gly Gly Gln Arg Asn Asp Val Tyr Leu Gly Pro
                355                 360

<210> SEQ ID NO 2
<211> LENGTH: 363
<212> TYPE: PRT
<213> ORGANISM: Mortierella alpina

<400> SEQUENCE: 2

Met Phe Ser Ser Met Arg Phe Lys Ala Arg Thr Arg Ser Leu Phe Leu
1               5                   10                  15

Ser Tyr Val Lys Asp Trp Gly Leu Val Ile Val Ile Leu Ala Val Phe
            20                  25                  30

Ser Tyr Val Asp Thr Leu Glu Pro Phe His Arg Gln Phe Ser Val Gln
        35                  40                  45

Asp Met Ser Ile Gln His Pro Tyr Ala Lys Lys Glu Thr Val Pro Val
    50                  55                  60

Trp Met Ala Leu Val Leu Ala Phe Ile Leu Pro Ala Val Val Ile Gly
65                  70                  75                  80

Leu Ile Ala Leu Leu Lys Arg Arg Ser Tyr Thr Asp Phe His Asn Gly
                85                  90                  95

Val Leu Gly Leu Phe Leu Thr Gln Ala Leu Val Leu Ile Val Thr Asp
            100                 105                 110

Ser Ile Lys Ile Ala Val Gly Arg Pro Arg Pro Asp Phe Leu Asp Arg
        115                 120                 125

Cys Leu Asp Leu Tyr Asp Asn Gln Ala Ala Gly Thr Pro Leu Gly Pro
    130                 135                 140

Leu Ser Asp Pro Ile Asn Met Leu Ser Asn Ser Thr Ile Cys Thr Arg
145                 150                 155                 160

Thr His Leu Leu Arg Asp Gly Phe Lys Ser Phe Pro Ser Gly His Ser
                165                 170                 175

Ser Phe Ser Phe Gly Gly Leu Gly Tyr Leu Ser Met Phe Leu Ala Gly
            180                 185                 190

Lys Leu His Leu Phe Asp Glu Arg Gly His Ile Tyr Lys Ser Val Val
```

```
                    195                 200                 205
Val Leu Ala Pro Leu Ile Val Ala Ala Leu Ile Ala Thr Ser Arg Val
    210                 215                 220

Asp Asp Tyr Arg His His Trp Gln Asp Val Thr Val Gly Ala Phe Ile
225                 230                 235                 240

Gly Ala Thr Phe Ala Ile Phe Ser Tyr Arg Gln Tyr Pro Ser Leu
                245                 250                 255

Ala Ser Ser Lys Ser Asp Cys Pro Phe Ala Pro Arg Ile Gly Lys Asp
            260                 265                 270

Glu His Leu Pro Ala Ala Leu Leu Pro His His His Ile His Arg His
                275                 280                 285

Asp Asn Glu Val Val Glu Ala Glu Asp Glu Val His Arg Glu Ser Phe
290                 295                 300

Leu Ser Asn Val Gly Gly Ala Gly Ser Asn Arg Ser His Glu Ser Leu
305                 310                 315                 320

Thr Gly Gly Thr Ser Leu Gln Asp Leu Ser Asn Asn His His Gly Ala
                325                 330                 335

Lys Leu Asn Ser Thr Ala Gly Tyr Gly Phe Asp Gln Gln Arg Asn Gly
            340                 345                 350

Gly Gly Gln Arg Asn Asp Val Tyr Leu Gly Pro
        355                 360

<210> SEQ ID NO 3
<211> LENGTH: 1092
<212> TYPE: DNA
<213> ORGANISM: Mortierella alpina

<400> SEQUENCE: 3
atgttctcgt ccatgcgctt caaggcccgg acaaggtcct tgtttctctc ctatgtcaag      60
gactggggtc tggtgattgt gatcctggcc gtcttctctt acgtcgacac actcgagcca     120
ttccatcgcc agttctctgt ccaagacatg tccattcagc atccctatgc aaagaaggag     180
acggttcctg tatggatggc gctggtactt gctttcattc tccccgctgt tgttattggg     240
cttattgccc tcctcaagag aagatcctac acggattttc acaacggagt acttggcctc     300
tttcttactc aggccctcgt tcttattgta actgacagca tcaagattgc tgttggcaga     360
cctcgtcctg actttctgga tcgctgcctt gacttgtacg ataaccaagc agcgggcaca     420
cccctaggac ctctctcgga tccaatcaac atgctatcaa actcgaccat tgcaccagg     480
acacacttgc tgagagatgg attcaaatcg ttccctcgg acattcctc cttttcattc     540
ggaggactgg gctacttgtc catgtttctt gcaggcaagc tgcatctgtt tgacgagcgt     600
ggacatatct ataaatcggt cgtagttctg gcgcctttga tcgtcgctgc tttgatcgct     660
acctcgcgcg tggacgacta caggcaccat tggcaggatg tcaccgtcgg agccttcatt     720
ggagccacat ttgccatctt ttcctaccgt cagtactacc cttccttggc gagttctaaa     780
tccgactgcc ccttcgcgcc tcgcattggc aaggacgagc atttgccggc agcactgttg     840
cctcatcacc atatccaccg acacgacaac gaggtggtgg aggcagagga cgaagtgcat     900
cgggaatcgt ttctgagtaa tgtcgggggc gcgggttcga atcggtctca cgagtctttg     960
acgggaggaa cgagtctgca ggatctgagt aacaatcatc atgggccaa gctcaacagc    1020
acggcgggct atggctttga tcagcagcgt aatggaggtg gtcaacggaa cgatgtatac    1080
ttgggaccat ga                                                       1092
```

```
<210> SEQ ID NO 4
<211> LENGTH: 1635
<212> TYPE: DNA
<213> ORGANISM: Mortierella alpina

<400> SEQUENCE: 4
atgttctcgt ccatgcgctt caaggcccgg acaaggtcct tgtttctctc ctatgtcaag      60
gactggggtc tggtgattgt gatcctggcc gtcttctctt acgtcgacac actcgagcca     120
ttccatcgcc agttctctgt ccaagacatg tccattcagc atccctatgc aaagaaggag     180
acggttcctg tatggatggc gctggtaagt gtttccaatc attttttccc gttttgttga     240
ctcgcgattc tcgtgtgct actgcttggt ttttttttccc catcctcatg gtgtggagtt     300
tggtctccag ccgtaaccac aaagcgcagt ctgtcccacg ctgcaccctt gtagaggac      360 aatggccatg gagcatgaag aatgagatta ctcatgcctc ttttttttcct ttttttcttcg    420 tcgtgttctg tgttgattca ggtacttgct ttcattctcc ccgctgttgt tattgggctt     480
attgccctcc tcaagagaag atcctacacg gattttcaca acggagtact tggcctcttt     540
cttactcagg ccctcgttct tattgtaact gacagcatca aggtaagcta ccaactcccc     600
ccctctcatg gctttctcct ttctttttttt ttgtatgcga tctttggact caagtgcgtt     660
gaaaaaaaag ggggggtaga ataatatgca acgtgaacaa tctctggaca gtgtttattt     720
cggggacact catcctctgg taactgtttt cagccaaaga gttccttcta ctagaactat     780
gactctcgac ttgatacaag gcggctgttg tttgtgttgg gcgcagatcc tttagtgaca     840
atagaacaaa gcgtactcat acctgttgtt ttcccttggt cgtgatagat tgctgttggc     900
agacctcgtc ctgactttct ggatcgctgc cttgacttgt acgataacca agcagcgggc     960
acacccctag gacctctctc ggatccaatc aacatgctat caaactcgac catttgcacc    1020
aggacacact tgctgagaga tggattcaaa tcgttcccct cgggacattc ctccttttca    1080
ttcggaggac tgggctactt gtccatgttt cttgcaggca agctgcatct gtttgacgag    1140
cgtggacata tctataaatc ggtcgtagtt ctggcgcctt tgatcgtcgc tgctttgatc    1200
gctacctcgc gcgtggacga ctacaggcac cattggcagg atgtcaccgt cggagccttc    1260
attggagcca catttgccat cttttcctac cgtcagtact acccttcctt ggcgagttct    1320
aaatccgact gccccttcgc gcctcgcatt ggcaaggacg agcatttgcc ggcagcactg    1380
ttgcctcatc accatatcca ccgacacgac aacgaggtgg tggaggcaga ggacgaagtg    1440
catcgggaat cgtttctgag taatgtcggg ggcgcgggtt cgaatcggtc tcacgagtct    1500
ttgacgggag gaacgagtct gcaggatctg agtaacaatc atcatggggc caagctcaac    1560
agcacggcgg gctatggctt tgatcagcag cgtaatggag gtggtcaacg gaacgatgta    1620
tacttgggac catga                                                    1635

<210> SEQ ID NO 5
<211> LENGTH: 1188
<212> TYPE: DNA
<213> ORGANISM: Mortierella alpina

<400> SEQUENCE: 5
cacgaggctc gtcgctgcca ccttgtacac actcacgcac atatcctgat ctagctgcct      60
atctactcgg gatcatgttc tcgtccatgc gcttcaaggc ccggacaagg tccttgtttc     120
tctcctatgt caaggactgg ggtctggtga ttgtgatcct ggccgtcttc tcttacgtcg     180
acacactcga gccattccat cgccagttct ctgtccaaga catgtccatt cagcatccct     240
```

```
atgcaaagaa ggagacggtt cctgtatgga tggcgctggt acttgctttc attctccccg    300
ctgttgttat tgggcttatt gccctcctca agagaagatc ctacacggat tttcacaacg    360
gagtacttgg cctctttctt actcaggccc tcgttcttat tgtaactgac agcatcaaga    420
ttgctgttgg cagacctcgt cctgactttc tggatcgctg ccttgacttg tacgataacc    480
aagcagcggg cacacccta ggacctctct cggatccaat caacatgcta tcaaactcga     540
ccatttgcac caggacacac ttgctgagag atggattcaa atcgttcccc tcggacatt     600 cctccttttc attcggagga ctgggctact tgtccatgtt tcttgcaggc aagctgcatc    660
tgtttgacga gcgtggacat atctataaat cggtcgtagt tctggcgcct ttgatcgtcg    720
ctgctttgat cgctacctcg cgcgtggacg actacaggca ccattggcag gatgtcaccg    780
tcggagcctt cattggagcc acatttgcca tcttttccta ccgtcagtac taccctccct   840
tggcgagttc taaatccgac tgccccttcg cgcctcgcat tggcaaggac gagcatttgc    900
cggcagcact gttgcctcat caccatatcc accgacacga caacgaggtg gtggaggcag   960
aggacgaagt gcatcgggaa tcgtttctga gtaatgtcgg gggcgcgggt tcgaatcggt   1020
ctcacgagtc tttgacggga ggaacgagtc tgcaggatct gagtaacaat catcatgggg   1080
ccaagctcaa cagcacggcg ggctatggct ttgatcagca gcgtaatgga ggtggtcaac   1140
ggaacgatgt atacttggga ccatgagcag atgaaacaaa ttgaaagg                1188
```

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      PAP2.2-1f primer

<400> SEQUENCE: 6
ttccgtcagg acactcctcc agt                                            23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      PAP2.2-4r primer

<400> SEQUENCE: 7
gacaatgccg aggatcgagc c                                              21

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      Eco-PAP2-2-F primer

<400> SEQUENCE: 8
gaattcatgt tctcgtccat gcgcttcaag                                     30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      Kpn-PAP2-2-R primer

<400> SEQUENCE: 9
tggtacctca tggtcccaag tatacatcgt tcc      33

<210> SEQ ID NO 10
<211> LENGTH: 366
<212> TYPE: PRT
<213> ORGANISM: Laccaria bicolor

<400> SEQUENCE: 10

```
Met Ala Phe Phe Gln Pro Ser His Ala Arg Thr Lys Val Pro Ala Met
1               5                   10                  15

Ser Pro Thr Arg Arg Lys Leu Val Phe Ser Tyr Ala Pro Asp Trp
            20                  25                  30

Tyr Ala Met Met Thr Ile Ala Leu Phe Phe Ser Leu Asp Lys Val Asn
                35                  40                  45

Gly Tyr Arg Arg Val Phe Ser Leu Glu Asp Thr Ser Leu Arg His Pro
        50                  55                  60

Tyr Ala Val His Glu Arg Val Pro Asn Ile Ala Leu Tyr Leu Ile Cys
65                  70                  75                  80

Phe Val Ser Pro Leu Leu Ile Gln Pro Val Ile Asn Phe Phe Thr Val
                85                  90                  95

Arg Ser Trp Trp Asp Phe His Asn Gly Ser Leu Gly Leu Val Leu Gly
            100                 105                 110

Leu Ala Leu Thr Gly Ser Val Thr Gln Phe Val Lys Ile Thr Val Gly
        115                 120                 125

Arg Pro Arg Pro Asp Val Ile Asp Arg Cys Gln Pro Thr Gly Ser
130                 135                 140

Val Asp Pro Thr Phe Gly Leu Ser Asn Trp Thr Ile Cys Thr Gln Ala
145                 150                 155                 160

Ser Glu Ala Ile Leu Arg Asp Gly Phe Arg Ser Phe Pro Ser Gly His
                165                 170                 175

Ser Ser Met Ser Phe Ala Gly Leu Gly Phe Leu Ser Phe Tyr Leu Ala
            180                 185                 190

Gly Lys Leu His Leu Phe Asp Ser Arg Gly His Thr Gly Lys Ala Trp
        195                 200                 205

Leu Ala Leu Ser Pro Phe Ala Gly Ala Ser Leu Val Ala Ile Ser Arg
    210                 215                 220

Thr Met Asp Tyr Arg His His Trp Gln Asp Val Leu Val Gly Ser Ile
225                 230                 235                 240

Leu Gly Thr Val Leu Ala Tyr Phe Ser Tyr Arg Gln Tyr Tyr Pro Ser
                245                 250                 255

Leu Glu Ser Asp Leu Ser His Arg Pro Tyr Ser Pro Arg Ile Lys His
            260                 265                 270

Asp Glu Glu Asp Gly Leu Pro Ile His Val Arg Thr Gly Ser Glu Ser
        275                 280                 285

His Ala Phe Ala His His Glu Ser Arg Thr Asn Pro Phe Leu Asn Thr
    290                 295                 300

Gln Ala Arg Asp Pro Glu Arg Tyr Thr Ser Phe Asp His Thr Asp Ala
305                 310                 315                 320

Glu Asp Phe Glu Leu Asp Gly Thr Val Pro Arg Pro Arg Ser Gly Ser
                325                 330                 335

Leu Glu Glu Ile Trp Lys Asp Asp Glu Thr His Ser Arg Met Gly Ser
            340                 345                 350
```

```
Pro Phe Val Asp Pro Phe Ala Thr Lys Thr Ser Thr Ala Leu
            355                 360                 365
```

<210> SEQ ID NO 11
<211> LENGTH: 289
<212> TYPE: PRT
<213> ORGANISM: Saccharomyces cerevisiae

<400> SEQUENCE: 11

```
Met Asn Arg Val Ser Phe Ile Lys Thr Pro Phe Asn Ile Gly Ala Lys
1               5                   10                  15

Trp Arg Leu Glu Asp Val Phe Leu Leu Ile Ile Met Ile Leu Leu Asn
            20                  25                  30

Tyr Pro Val Tyr Tyr Gln Gln Pro Phe Glu Arg Gln Phe Tyr Ile Asn
        35                  40                  45

Asp Leu Thr Ile Ser His Pro Tyr Ala Thr Thr Glu Arg Val Asn Asn
    50                  55                  60

Asn Met Leu Phe Val Tyr Ser Phe Val Val Pro Ser Leu Thr Ile Leu
65                  70                  75                  80

Ile Ile Gly Ser Ile Leu Ala Asp Arg Arg His Leu Ile Phe Ile Leu
                85                  90                  95

Tyr Thr Ser Leu Leu Gly Leu Ser Leu Ala Trp Phe Ser Thr Ser Phe
            100                 105                 110

Phe Thr Asn Phe Ile Lys Asn Trp Ile Gly Arg Leu Arg Pro Asp Phe
        115                 120                 125

Leu Asp Arg Cys Gln Pro Val Glu Gly Leu Pro Leu Asp Thr Leu Phe
    130                 135                 140

Thr Ala Lys Asp Val Cys Thr Thr Lys Asn His Glu Arg Leu Leu Asp
145                 150                 155                 160

Gly Phe Arg Thr Thr Pro Ser Gly His Ser Ser Glu Ser Phe Ala Gly
                165                 170                 175

Leu Gly Tyr Leu Tyr Phe Trp Leu Cys Gly Gln Leu Leu Thr Glu Ser
            180                 185                 190

Pro Leu Met Pro Leu Trp Arg Lys Met Val Ala Phe Leu Pro Leu Leu
        195                 200                 205

Gly Ala Ala Leu Ile Ala Leu Ser Arg Thr Gln Asp Tyr Arg His His
    210                 215                 220

Phe Val Asp Val Ile Leu Gly Ser Met Leu Gly Tyr Ile Met Ala His
225                 230                 235                 240

Phe Phe Tyr Arg Arg Ile Phe Pro Pro Ile Asp Asp Pro Leu Pro Phe
                245                 250                 255

Lys Pro Leu Met Asp Asp Ser Asp Val Thr Leu Glu Glu Ala Val Thr
            260                 265                 270

His Gln Arg Ile Pro Asp Glu Glu Leu His Pro Leu Ser Asp Glu Gly
        275                 280                 285

Met
```

<210> SEQ ID NO 12
<211> LENGTH: 372
<212> TYPE: PRT
<213> ORGANISM: Mortierella alpina

<400> SEQUENCE: 12

```
Met Gly Cys Phe Ala Arg Lys Thr His Thr Thr Pro His Pro Asp Thr
1               5                   10                  15

Asn Thr Thr Ala Val Asn Gly His His Asn Val Tyr Ser Met Gln Thr
```

```
                    20                  25                  30
Arg Pro Lys Phe Gly Gln Trp Leu Lys Cys Thr Trp Leu Asp Ile Leu
        35                  40                  45
Thr Met Ala Val Met Gly Ala Leu Gly Leu Gly Val Tyr Met Leu Arg
    50                  55                  60
Pro Val Pro Asn Arg Ser Phe Ala Val Thr Phe Ala Asp Gly Glu Ile
65                  70                  75                  80
Val Tyr Pro Glu Phe Ala Tyr Pro Leu Arg Lys Glu Ile Val Pro Ile
                85                  90                  95
Trp Leu Ala Ser Phe Leu Ala Val Val Pro Val Leu Gly Ile Leu
                100                 105                 110
Leu Met Gln Ile Arg Val Arg Ser Phe Trp Asp Val Asn Asn Ala Ile
        115                 120                 125
Val Gly Leu Leu Tyr Ser Leu Ile Thr Ala Ala Val Phe Gln Val Phe
    130                 135                 140
Ile Lys Trp Leu Ile Gly Gly Leu Arg Pro His Phe Leu Glu Val Cys
145                 150                 155                 160
Lys Pro Asp Thr Ser Leu Ala Thr Asp Ala Gly Tyr Asn Arg Lys Gly
                165                 170                 175
Phe Gln Gln Gln Tyr Phe Thr Arg Glu Ile Cys Thr Gly Asp Glu Lys
                180                 185                 190
Glu Ile Asn Asp Ser Leu Glu Ser Phe Pro Ser Gly His Ser Thr Ala
        195                 200                 205
Ala Phe Ala Gly Phe Val Phe Leu Tyr Leu Tyr Leu Asn Ala Lys Leu
    210                 215                 220
Lys Val Phe Ser Asn Tyr His Pro Ala Met Trp Lys Leu Ile Val Ile
225                 230                 235                 240
Tyr Thr Pro Ile Leu Gly Ala Val Leu Ile Gly Gly Ala Leu Thr Ile
                245                 250                 255
Asp Glu Phe His Asn Trp Tyr Asp Val Val Ala Gly Ala Ile Ile Gly
                260                 265                 270
Ser Val Met Ala Phe Ser Ser Tyr Arg Met Thr Tyr Ala Ala Ile Trp
        275                 280                 285
Asp Trp Arg Tyr Asn His Ile Pro Leu Asn Arg Asn Ala Pro Phe Pro
    290                 295                 300
Phe Leu Arg Asp Ser Gly Asp Leu Val Gly Ala Val Phe Thr Arg Lys
305                 310                 315                 320
Ala Gly Trp Gly Asp Ala Ala Lys Val Pro Glu Arg Gly Asn Asp Trp
                325                 330                 335
Asn His His Gly Gln Thr Pro Asn Ala Asn Gln Asp Gly Tyr Gln Ala
                340                 345                 350
Ser Ser Ser Ile Pro Leu Arg Ser Val Gly Gly Gly Gln Ala Gln Pro
        355                 360                 365
Glu Asn Ile Val
    370
```